United States Patent
Gorenstein (12)

(10) Patent No.: US 6,694,265 B2
(45) Date of Patent: Feb. 17, 2004

(54) METHOD AND APPARATUS FOR DETERMINING THE BOUNDARIES OF A DETECTOR RESPONSE PROFILE AND FOR CONTROLLING PROCESSES

(75) Inventor: Marc V. Gorenstein, Needham, MA (US)

(73) Assignee: Waters Investments Limited, Delaware, MA (US)

( * ) Notice: Subject to any disclaimer, the term of this patent is extended or adjusted under 35 U.S.C. 154(b) by 205 days.

(21) Appl. No.: 09/949,199

(22) Filed: Sep. 7, 2001

(65) Prior Publication Data

US 2002/0052701 A1 May 2, 2002

Related U.S. Application Data

(60) Provisional application No. 60/232,297, filed on Sep. 8, 2000.

(51) Int. Cl.$^7$ .............................................. G06F 19/00
(52) U.S. Cl. ............................................ 702/22; 703/2
(58) Field of Search ........................... 702/66, 67, 69, 702/70, 71, 73, 74, 124, 126, 179, 183, 189, 193, 194, FOR 103, FOR 104, FOR 110, FOR 134, FOR 170, 22, 30, 31, 35, 45; 703/1, 2, 6

(56) References Cited

U.S. PATENT DOCUMENTS

| | | | | |
|---|---|---|---|---|
| 3,746,982 A | * | 7/1973 | Allington et al. | 324/76.18 |
| 3,813,532 A | * | 5/1974 | Sato et al. | 708/823 |
| 4,450,497 A | * | 5/1984 | Bignell | 361/82 |
| 4,541,275 A | * | 9/1985 | Kerzner | 73/152.02 |
| 4,544,489 A | | 10/1985 | Campbell et al. | 210/709 |
| 4,899,575 A | * | 2/1990 | Chu et al. | 73/54.08 |
| 5,969,228 A | | 10/1999 | Gorenstein | 73/23.22 |
| 6,283,379 B1 | * | 9/2001 | Kazamierowicz et al. | 236/15 BC |

OTHER PUBLICATIONS

Grushka et al., "Slope Analysis for Recognition and Characterization of Strongly Overlapped Chromatographic Peaks", Analytical Chemistry, vol. 44, No. 3, Mar. 1972, ppg: 484–489.

Normal Dyson, "Chromatographic Integration Methods", $2^{nd}$ Edition (Aug. 1998), 111 pages.

* cited by examiner

*Primary Examiner*—Marc S. Hoff
*Assistant Examiner*—Mohamed Charioui
(74) *Attorney, Agent, or Firm*—Brown, Rudnick, Berlack & Israels, LLP.; Brian Michaelis; John Serio

(57) ABSTRACT

An improved method and apparatus for identifying peaks and for determining the boundaries of those peaks, and boundaries of multiple peaks and shoulders within chromatograms. The method and apparatus effects real time identification and determination of the boundaries of these peaks for the purpose of fraction collection. The method and apparatus determines the boundary of a peak within a detector response profile that comprises data points plotted graphically on an X and Y-axis wherein the X-axis represents a first variable and the Y-axis represents a second variable, each variable having a value. The plot at each of the data points has a slope. Data points having a slope which deviates from a consistent value define a peak, and data points having a slope with a consistent value define a baseline.

21 Claims, 20 Drawing Sheets

|  | NOTINPEAK | DETECTSTART | INPEAK | DETECTEND |
|---|---|---|---|---|
| NOTINPEAK | X | X |  |  |
| DETECTSTART |  |  | X |  |
| INPEAK |  |  | X | X |
| DETECTEND | X |  |  |  |

| STATE | NOT INPEAK | DETECT UPSLOPE START | IN UPSLOPE | D2APEX | DETECT D2APEX | IN DNSLOPE | DETECT ENDFROM APEX | IN TAIL | DETECT ENDFROM INFLECT |
|---|---|---|---|---|---|---|---|---|---|
| NOTINPEAK | X | | | | | | | | |
| DETECTUP SLOPESTART | | | X | | | | | | |
| INUPSLOPE | | | X | X | | | | | |
| D2APEX | | | | | X | | | | |
| DETECT D2APEX | | | | | | X | | | |
| INDNSLOPE | | | | | | X | X | | |
| DETECT END FROMAPEX | | | | | X | | | X | |
| INTAIL | | | | | X | | | X | X |
| DETECT END FROMINFLECT | X | | | | | | | | |

FIG. 16

METHOD AND APPARATUS FOR DETERMINING THE BOUNDARIES OF A DETECTOR RESPONSE PROFILE AND FOR CONTROLLING PROCESSES

This application claims the benefit of provisional application 60/232,297 filed on Sep. 8, 2000.

FIELD OF INVENTION

The present invention is directed to detectors, and more particularly to methods and apparatus for determining the boundaries of a detector response profile.

BACKGROUND OF THE INVENTION

Detectors and sensors are used in industry and in research to determine the presence or absence of a molecule, material, chemical, objects or a change in a physical parameter of the environment around or in contact with the detector. By way of example, a thermometer senses changes in temperature. If viewed over time, temperature, one variable, having a value in degrees, can be compared to a second variable, time, measured in seconds, minutes or years. These variables can be graphed or plotted.

As used herein, the term "detector" is used to refer to any instrument or device which creates a signal in response to the presence or absence of a molecule or a change in a physical parameter of the environment in contact with the instrument or device. Common detectors used in industry and research include absorbance detectors, fluorescence detectors, mass spectrometry detectors, chemi-luminescence detectors, refractometry detectors, viscometry detectors, radiation detectors and thermometers.

As used herein, the word "profile" refers to a depiction of a plot of data points usually with lines drawn between the data points whether in electronic form or printed. A "plot" refers to graphical organization of a series of data points, in electronic and printed forms. Such a plot is normally presented on an X-axis and an Y-axis where each axis represents one variable. Typically detectors measure responses at a uniform sample rate. Thus the time difference between adjoining data points is a constant that is termed the sample period. Typically, a plot of data points from a detector will have data points associated with no activity, which result in consistent readings or consistent slope. These consistent readings, representative of no activity or change, are referred to as a baseline. A change in the environment surrounding the detector will alter the profile of the plot creating a "peak" or "valley." As used herein, the word "peak" refers to any change in the profile, whether plotted as an upwardly projecting or downwardly descending plot. Whether the plot is directed up or down is a matter of choice and the present discussion will address each as a peak for the convenience of clarity. The words plot and profile, as used herein, are not intended to be limited to visually perceived representations. Rather, the words are used to represent how data points are managed or processed to depict information.

Chromatography is the science of separation based upon specific or nonspecific binding of molecules to a stationary phase. Aspects of the present invention have special application in gas and liquid chromatography. In liquid chromatography, a liquid carrying one or more compositions of interest is carried through a solid phase. The compositions elute from the solid phase at different times producing changes in one or more physical parameters measured by the detector. These changes are plotted over time and such graphical representations are known as a chromatograph.

Chromatographs typically exhibit peaks that correspond to the compounds that have been separated. It is often desirable to direct fluids containing the compounds to vessels or further processes. By way of example, it may be useful to direct a fluid containing a compound, determined by absorbance, to a mass spectrometer to determine its molecular weight. Also, it may be useful to collect the fluid defining a separated peak into a collection vial. This is an operation known as "fraction collection." Thus, chromatographic instruments often are equipped with valves for directing compounds from the common stream.

It is accepted practice to analyze a peak in order to obtain two response factors, peak height and peak area. Each of these factors gives a response that is in proportion to the amount of material injected onto the column. But the height and area can be obtained only when the underlying baseline of a peak and the start time and stop time of the peak are known. Ideally a chromatogram consists of a series of peaks, with all pairs separated by a region of baseline. These peaks are termed baseline-resolved peaks. Chromatographs, however, can be complex. A peak from a compound may appear within a cluster of peaks, or merge with other peaks, or appear not as a well-defined peak, but as a shoulder.

In the case of a baseline-resolved peak, the boundaries of the peak are taken to be the start and stop times of the peak's baselines. The start time, also known as "lift-off," is when the peak first appears above the baseline response. The stop time, also known as "touchdown," is when the peak response becomes coincident with the baseline response. These times determine the baseline drawn under the peak, which is needed for the determination of height and area. It is useful to determine height and area with computers equipped with appropriate software, such as software including an integration algorithm. For the integration algorithm to be useful, it must determine lift-off and touchdown accurately and reproducibly for peaks of varying heights, and shape asymmetries.

Unfortunately, the times of "liftoff" and "touchdown" are dependent on the height of the peak. As the height of the peak changes, the position of "lift-off" and "touchdown" change. The higher the peak, the further apart these points become. Therefore, dependence on peak height is undesirable, as it requires the practitioner to find a compromise value, or to change the value as the peak heights change. Further, the results, using prior art methods, are dependent on the baseline slope. If the slope of the baseline changes, the position of "lift-off" and "touchdown" change. Problems with this dependence on the baseline slope become significant in the case of small peaks. In the case of small peaks, positive slopes yield start and stop times that occur earlier and negative slopes yield start and stops times that occur later.

In the case of a cluster, the baseline start time is the liftoff time for the first peak in a cluster, and the baseline stop time is the touchdown time for the last peak in the cluster. Their lift off and touch down points must be determined with the presence of adjacent peaks of varying heights and resolutions and shape asymmetries.

Once lift-off and touchdown are established, the next step is to determine boundaries between peaks in a cluster. If a valley separates a pair of peaks, the determination of the boundary is straightforward. Valleys are the local minima between peak apices. The point at the minimum of the valley is the boundary, defining the stop time of the prior peak and the start time of the following peak.

The identification of an appropriate peak boundary for a shoulder is a more difficult problem. A shoulder occurs when two peaks co-elute with low enough resolution such that there is no valley between the peak apices. The shoulder cannot be detected separately from the main peak because there is no valley point separating them. Further, even if the apex of the shoulder is identified, there is no obvious means to demarcate the shoulder from the adjoining peak. The demarcation between the main peaks and the shoulder is hard to define and there is no accepted method within the prior art to demarcate a shoulder from an adjoining peak.

Accurate and reliable determination of lift-off and touch down is essential to accurate and reliable quantitation. Lift-off and touch-down establish a baseline, and it is the baseline that affects all subsequent determinations of peak heights and areas. Accuracy is compromised if the determination of baseline is erroneous or non-reproducible.

The data analysis problem for fraction collection is similar to problems found in quantitation, in that peak boundaries must be determined. Fraction collection, however, because of its real time nature, requires an algorithm that operates in real time. It must be able to handle a wide variety of situations reliably, such as can occur with peaks whose concentrations are so high as to saturate the detector.

The goal of a fraction collection algorithm is to identify times at which a valve should be opened and closed. In collecting fractions, one may want to recover one hundred (100) percent of a material, or one may only want to collect the most concentrated material in the heart of a peak. To achieve one hundred percent collection the collection valve should open at or near lift-off and close at or near touch-down. If one wants to collect in the heart of the peak, the collection valve needs to open later and close sooner. A robust fraction collection algorithm must be able to reproducibly identify in real time a variety of features in the peak.

The simplest known scheme for fraction collection is to trigger collection on a response threshold, however, this prior art method will not collect low-level peaks such that all responses fall below the threshold. While reducing the threshold will detect lower-level peaks, an unstable baseline may cause whole clusters to be collected or missed.

Another approach of the prior art for fraction collection is to trigger collection on slope thresholds. While this is an improvement over the response threshold, unpredictable results may still occur with low-level peaks on unstable baselines. Other problems with slope threshold arise due to the interaction between peak height and slope threshold. For a given value of slope threshold, the fraction of the peak collected decreases as the peak height drops. For a given peak height, the fraction of the peak collected decreases as the threshold rises. An additional problem with using slope thresholds to collect fractions is that shoulders can not be separately collected using this method.

SUMMARY OF THE INVENTION

The present invention provides an improved method and apparatus for identifying peaks and for determining the boundaries of those peaks, and boundaries of multiple peaks and shoulders within chromatograms. The method and apparatus effects more accurate identification and determination of the boundaries of these peaks for the purpose of quantitation. The method and apparatus also effects real time identification and determination of the boundaries of these peaks for the purpose of fraction collection. The boundaries of the detector response profile are used to control processes, including directing the flow of fluids, controlling heating or cooling, altering the course of chemical reactions and the like. These boundaries can also be used to extract quantitative information about the profile, such as the computation of the profile's area between boundaries.

Embodiments of the present invention are directed to methods and apparatus for determining the boundary of a peak within a detector response profile. The profile comprises data points plotted graphically on an X and Y-axis wherein the X-axis represents a first variable and the Y-axis represents a second variable, each variable having a value. The plot at each of the data points has a slope. Data points having a slope which deviates from a consistent value define a peak, and data points having a slope with a consistent value define a baseline.

The inventive method comprises the step of determining the presence of a peak having an apex and two sides. The method further comprises the step of selecting a first data point from a plurality of data points on one side of the apex of the peak, and selecting a second data point from a plurality of data points on a side of said peak opposite the side containing the first data point. The first data point and second data point have a position on the plot with one or more distal data points. The distal data points are further removed from the apex. One or more proximal data points are closer to or are at the apex. The plot at the first data point has a first slope and the plot at the second data point has a second slope.

The method further comprises the step of comparing the first and second slopes to the slope of the line extending between such first and second data points. If the first slope and the second slope are both equal to, or are both within a selected value of, the slope of a line extending between such first and second data points, then such first and second data points are baseline and such first and second data points define the boundary of a peak. Accordingly, the process terminates.

If the first slope and second slope have a different value from the slope of a line extending between the first and second data points, one distal data point is selected and the slope of the plot at the selected distal data point is determined. If this distal data point is on the same side of the apex as the first data point, this distal data point becomes the new first data point. If this distal data point is on the same side of the apex as the second data point, this distal data point becomes the new second data point. The method then returns to the previous step that compares the slope at these two points to the slope of the line joining these two points.

The process iterates until the slope of the plot at such distal data points are of equal or within the selected value to a line extending there between. Such data points are baseline data points which define a baseline and define the boundary of the peak.

In one embodiment, the distal data point is selected as the distal data point proximal to the first or second data point having a slope which exhibits the greatest deviation from the slope of the line extending between the first and second data points.

The peak is determined by computing the second derivative of the plot to form a second derivative plot and identifying a minimum of the second derivative plot. The minimum of the second derivative plot corresponds to the apex of the peak of the plot.

The inventive method has application wherein the peak corresponds to a chemical entity flowing through a conduit, and the conduit has one or more valves that can direct the chemical entity to a further conduit, vessel or vent. The determination of the peak boundary allows the step of opening one or more valves to direct said chemical entity into the further conduit, vessel or vent with greater accuracy and reproducibility.

A further embodiment of the inventive method comprises an apparatus for processing detector response profiles. The profiles comprise a plot of data points plotted graphically on an X and Y-axis wherein the X-axis represents a first variable and the Y-axis represents a second variable, each variable having a value. The plot at each of the data points has a slope, wherein the data points having a slope which deviates from a consistent value define a peak and data points having a slope with a consistent value define a baseline.

The inventive method further comprises an apparatus having computing means for identifying a boundary of a peak. The computing means determines the presence of a peak, which peak has an apex and two sides. The computing means selects a first data point from a plurality of data points on one side of the apex of the peak and a second data point from a plurality of data points on a side of the peak opposite the side containing the first data point. The first data point and the second data point have a position on the plot with one or more distal data points. The distal data points are further removed from the apex and one or more proximal data points are closer to or are at the apex. The plot at the first data point has a first slope and the plot at the second data point has a second slope.

The computing means compares the first and second slopes to the slope of the line extending between such first and second data points. If the slope of the plot at the first data point and the second data point are equal to the slope of a line extending between such points or within a selected value, such points are baseline data points and such points define the boundary of the peak. Accordingly, the process terminates.

Where the first slope and second slope have a different value from the slope of a line extending between the first and second data points or the selected value, the computing means selects one distal data point and determines the slope of the plot at the selected distal data point. If this distal data point is on the same side of the apex as the first data point, this distal data point becomes the new first data point. If this distal data point is on the same side of the apex as the second data point, this distal data point becomes the new second data point. The computing means returns to the previous step that compares the slope at these two points to the slope of the line joining these two points.

In the event such slopes are not equal or within the selected value, computing means repeats the step of the preceding paragraph, until the slope of the plot at such distal data points are of equal or within the selected value to a line extending there between. Such data points are baseline data points which define a baseline and such data points define the boundary of said peak.

Computing means of the apparatus selects the distal data point as the distal data point proximal to the first or second data point having a slope which exhibits the greatest deviation from the slope of the line extending between the first and second data points.

Computing means of the apparatus determines the presence of the peak by computing the second derivative of the plot to form a second derivative plot and identifying a minimum of the second derivative plot. The minimum of the second derivative plot corresponds to the apex of the peak of the plot.

The apparatus of the present invention is illustratively a chromatographic instrument wherein said detector response profiles are chromatograms. Computing means can comprise a computer or a processor unit programmed to perform in the manner above.

In an illustrative embodiment, the apparatus comprises one or more conduits, control means and valves. The peak corresponds to a chemical entity flowing through one of the conduits having one or more valves that can direct the chemical entity to a further conduit, vessel or vent. Valve control means is in communication with computing means to receive a signal corresponding to the peak. Valve control means opens one or more valves to direct the chemical entity into the further conduit, vessel or vent in response to a signal from the computing means to open or close the valve(s). Valve control means may comprise a further computer or processor unit or the same computer or processor unit as the computing means.

Another embodiment of the invention is directed to a method and apparatus for determining the presence of a peak of a detector response profile. Again, the profile comprises a plot of data points plotted graphically on an X and Y-axis wherein the X-axis represents a first variable and the Y-axis represents a second variable, each variable having a value. The plot at each of the data points has a slope wherein the data points having a slope which deviates from a consistent value define a peak and data points having a slope with a consistent value define a baseline. The method comprises the step of, and the apparatus comprises computing means for, computing the second derivative of the plot to form a second derivative plot and identifying a minimum of the second derivative plot. The minimum of the second derivative plot corresponds to the apex of the peak of the plot.

A further embodiment of the invention is directed to a one-point-tangent method for demarcating the boundary between a shouldered peak and an adjoining peak. There are two implementations of this method. The apex method comprises connecting a line from a point on an apex to a downside point on the down-slope side of the apex. The slope of the profile at the downside point equals the slope of the line. The line is tangent to the peak profile at the point of contact. In this further embodiment, the algorithm for finding the tangent point is straightforward. The initial line connects the apex to the down-slope inflection point. The point on the apex remains fixed while the point on the inflection point is moved away from the apex sample point by sample point. As the point moves away the slope of the line becomes larger resulting in a decrease of the slope at the contact point. When the slope of the line is equal to or greater than the slope at the contact point the line is fixed.

The inflection point method comprises connecting a line from a point on an upslope inflection point to a downside inflection point on the down-slope side of the apex. The slope of the profile at the downside point equals the slope of the line. The line is tangent to the peak profile at the point of contact. In this further embodiment, the algorithm for finding the tangent point is straight forward. The initial line connects the up-slope inflection point to the down-slope inflection point. The point on the upslope inflection point remains fixed while the point on the down slope inflection point is moved away from the apex sample point by sample point. As the point moves away the slope of the line becomes larger resulting in a decrease of the slope at the contact point. When the slope of the line is equal to or greater that the slope at the contact point the line is fixed.

Features of the invention include provision of methods and apparatus that can locate a peak that is independent of the slope of the underlying baseline and independent of the height of the peak.

BRIEF DESCRIPTION OF THE DRAWINGS

The foregoing and other features and advantages of the present invention will be more fully understood from the following detailed description of illustrative embodiments, taken in conjunction with the accompanying drawings in which:

FIG. 16 is a table showing a complete set of states and a matrix of allowed transition states.

DETAILED DESCRIPTION OF THE INVENTION

The present disclosure will be described in detail with respect to chromatographic applications with the understanding that embodiments of the present invention are directed to industrial and process control applications as well.

It is an accepted practice to analyze a chromatographic peak in order to obtain two response factors: peak height and peak area. Each of these factors gives a response that is in proportion to the amount of material injected on to a chromatography column. However, the height and area of a chromatographic peak can be obtained only when the underlying baseline of the peak is known and the start and stop times of the peak can be ascertained.

It is contemplated within this disclosure that the identification of the lift-off and touchdown points can be more accurately determined for isolated peaks, peak clusters and the boundaries of peak shoulders. It is further contemplated within this disclosure that the detection of boundaries of peak shoulders can be more accurately determined and that this accurate determination can enable more precise fraction collection.

In the analysis of an isolated peak, the inventive method, like the prior art, finds a straight line whose end points connect two points on a chromatographic peak. The two points are the lift-off and touchdown points and the straight line is the baseline for the peak.

Figure 1A:
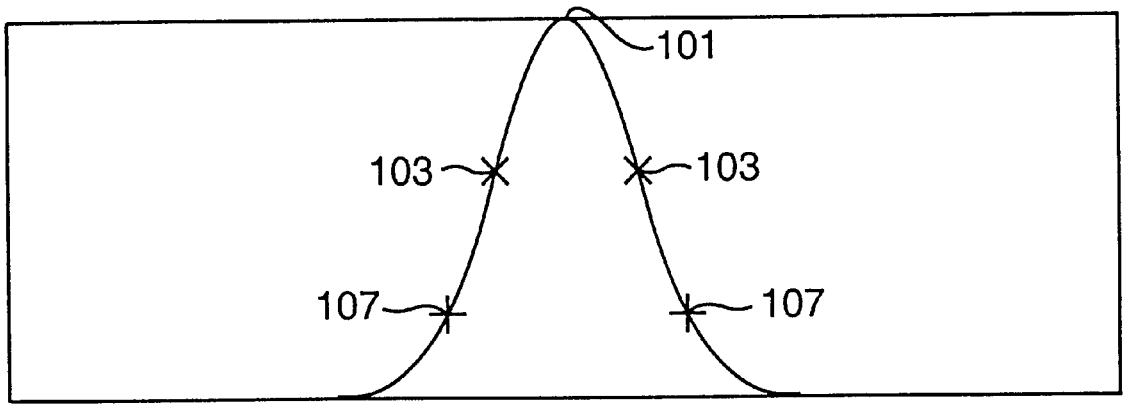
FIG. 1A shows an apex of the peak.
Figure 1B:
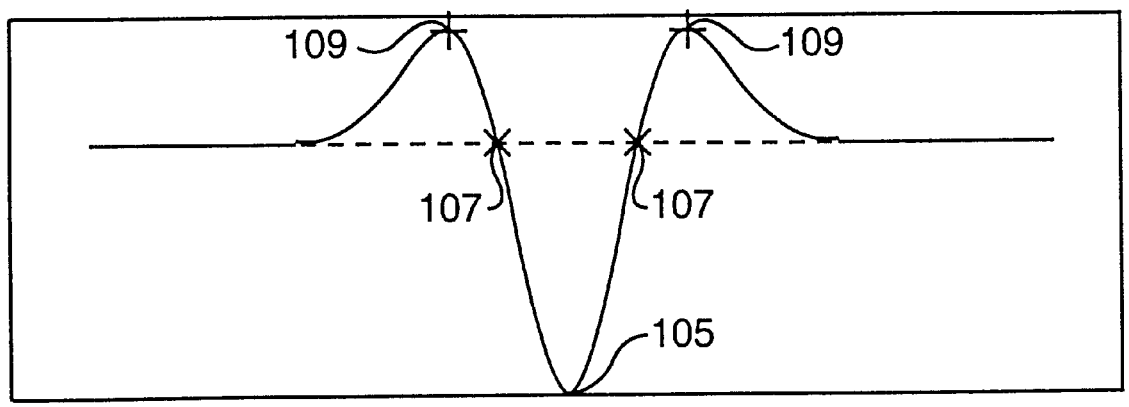
FIG. 1B shows a corresponding minimum of the second derivative of a peak.

The apex of a chromatographic peak is a local minimum of curvature. The second derivative measures the curvature of the profile at each point in time. In the inventive method the local minimum of the second derivative is used to detect a peak and to locate the peak's apex. The detection of a peak by the use of the second derivative allows detection even when a peak is shouldered; one can detect and locate the shoulder's apex by finding the local minimum in the second derivative. The inventive method requires that the magnitude of the $2^{nd}$ derivative at the local minimum be larger than a threshold value for a detection to be valid. Within the up-slope and down-slope straddling the apex of the peak there are always two inflection points. These inflection points denote the transitions between positive and negative curvature. As shown in FIG. 1A these inflection points 103 are illustrated on an isolated Gaussian peak. An apex of the peak 101 is depicted. Turning to FIG. 1B a corresponding minimum 105 of the second derivative of the peak 101 is shown. The point with the largest magnitude of the second derivative corresponds to the peak apex. The inflection points 103 in FIG. 1A correspond to the zero crossings 107 of the second derivative in FIG. 1B. Also shown in FIGS. 1A and 1B are local maxima 109 of the positive second derivative.

Figure 2A:
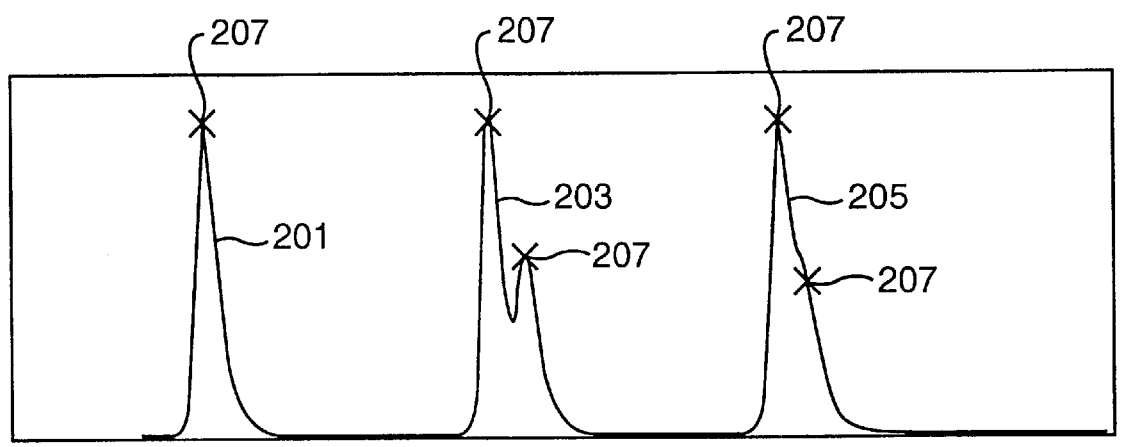
FIG. 2A shows an example of an isolated peak, a two-peak cluster, and a two-peak cluster with a shoulder.
Figure 2B:
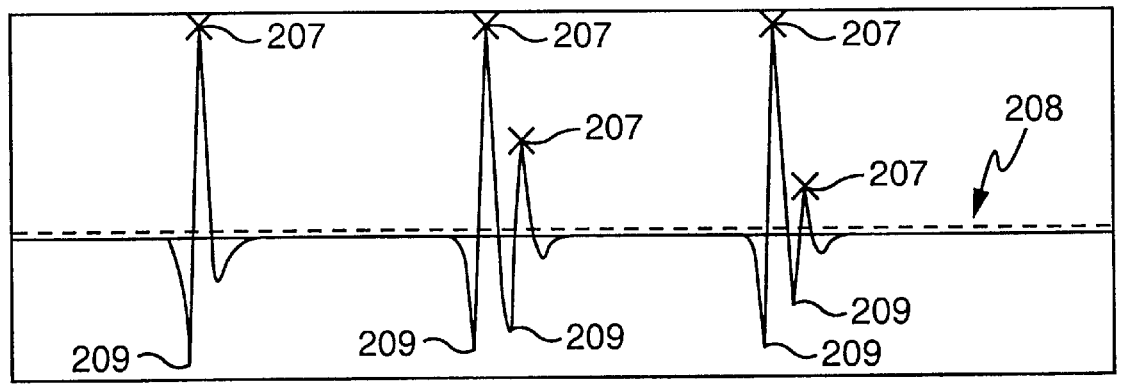
FIG. 2B shows a second derivative, a threshold line and a local maxima for each peak depicted in FIG. 2A.

In chromatograms that contain fused peaks, although not readily apparent, an apex and inflection points exist. Shown in FIG. 2A are examples of an isolated peak 201, a two-peak cluster 203, and a two-peak cluster with a shoulder 205. FIG. 2B shows a second derivative 209, a threshold line 208 and a local maxima 207 for each peak. The sign of the second derivative is changed so that the local maxima 207 correspond to the peak apex. The inventive method, as described hereinafter, detects peaks by obtaining the second derivative of a chromatogram and then locating the local maxima of the negative of the second derivative. When the local maxima of the negative of the $2^{nd}$ derivative profile is located, the two adjoining zero-crossing points identify the inflection points associated with that peak. The inflection points are used in the inventive method to find the peak baseline using a two-point tangency method set forth below.

The two-point tangency method is initiated with a trial baseline drawn between two points. In an illustrative embodiment one point is on the up-slope and one is on the down-slope both of which are above the actual baseline. Finding the second derivative apex and finding the inflection points associated with this apex determines these points. The trial baseline is the straight line connecting these two points. Although this straight line is not the final baseline, the inventive method uses these points and this straight line as an initial approximation of the final baseline.

An algorithm is used, within the inventive method, that allows one to start with the initial baseline and arrive at the final best estimate of the baseline. The algorithm gradually separates the end points such that the final pair of points is the baseline. In the inventive method a slope threshold determines the final pair of points. The two-point tangency method sets this threshold equal to zero. The algorithm takes the initial pair of points that connect the inflection points and subjects them to the following method:

1) The slope of the peak profile is determined at the two end points of the line. The slope of the line connecting these points is determined.
2) Two differences are formed. The first difference is the difference between the peak slope on the upslope at the first end-point minus the slope of the line. The second difference is the difference between the peak slope on the down slope at the last end-point minus the slope of the line. For the initial estimate, both these differences will be positive.
3) The end point with the larger difference is identified. If that difference is greater than zero, then that point is moved outward by one sample point, and the method continues with step 4. If the difference is less than zero, no further adjustments are made. The point determination process is finished. The start and stop times of the baseline is now determined as the final two points.
4) The two new points determine a new baseline.
5) Return to step one.

Figure 3A:
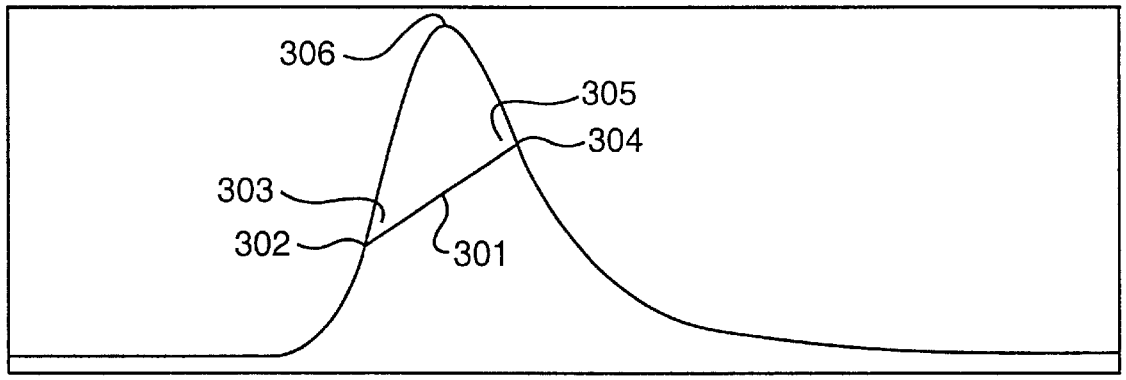
FIG. 3A shows a line connecting two inflection points and a point on the up-slope and a point on the down-slope of an apex.
Figure 3B:
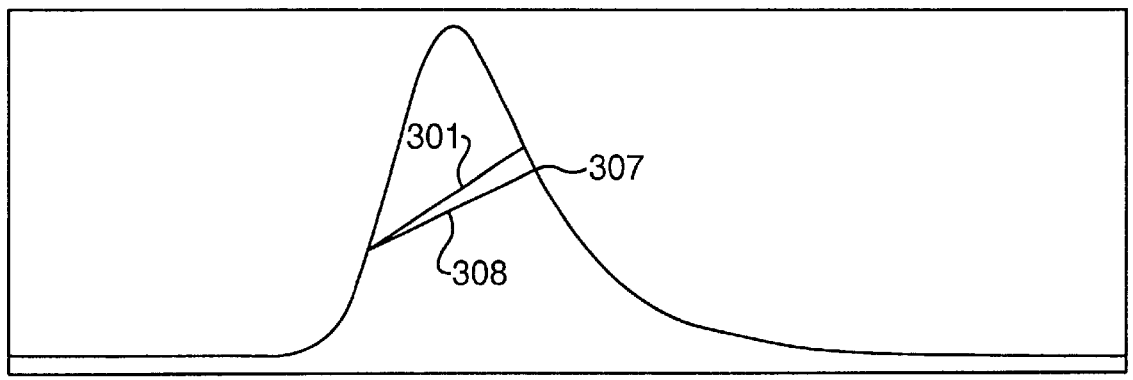
FIG. 3B shows a selection of points having the same up-slope point as in FIG. 3A and a new down-slope point.
Figure 3C:
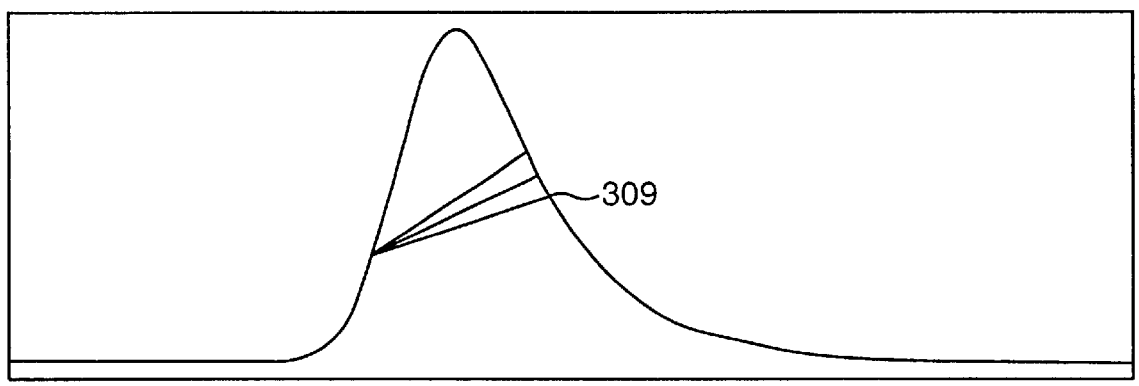
FIG. 3C shows a selection of points having the same up-slope point as in FIG. 3B and a new down-slope point.
Figure 3D:
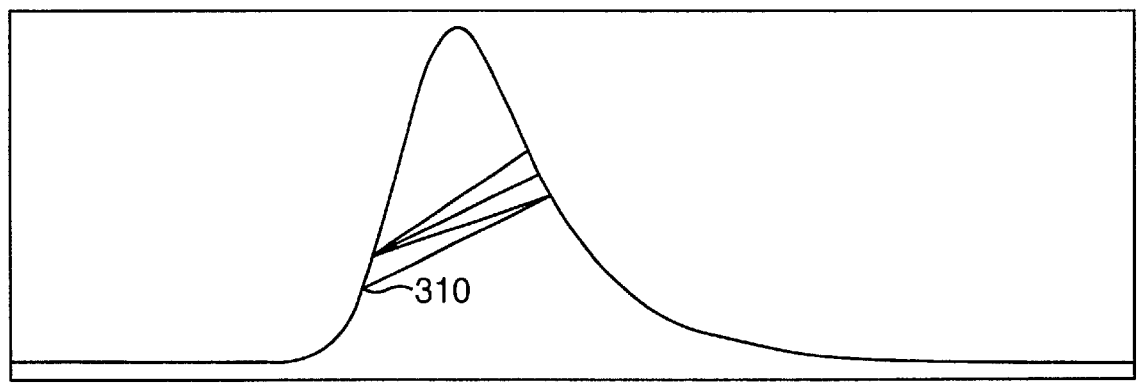
FIG. 3D shows a selection of points having the same down-slope point as in FIG. 3C and a new up-slope point.
Figure 3E:
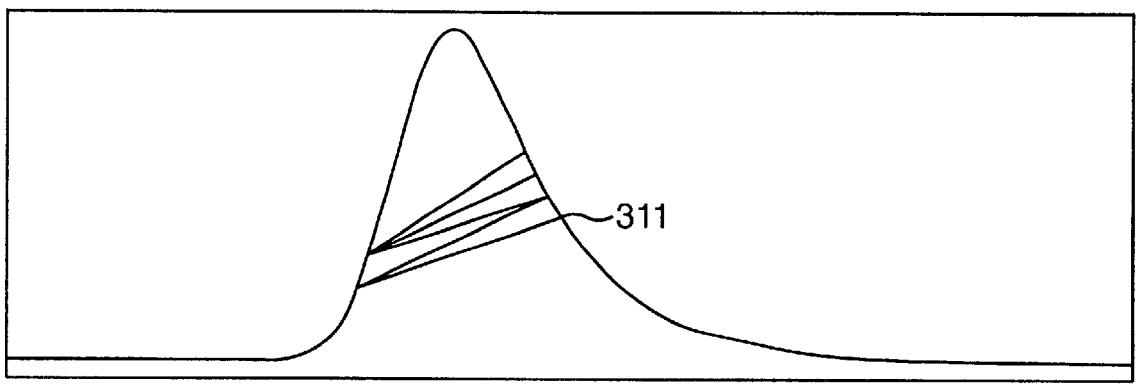
FIG. 3E shows a selection of point having the same up-slope point as in FIG. 3D and a new down-slope point.
Figure 3F:
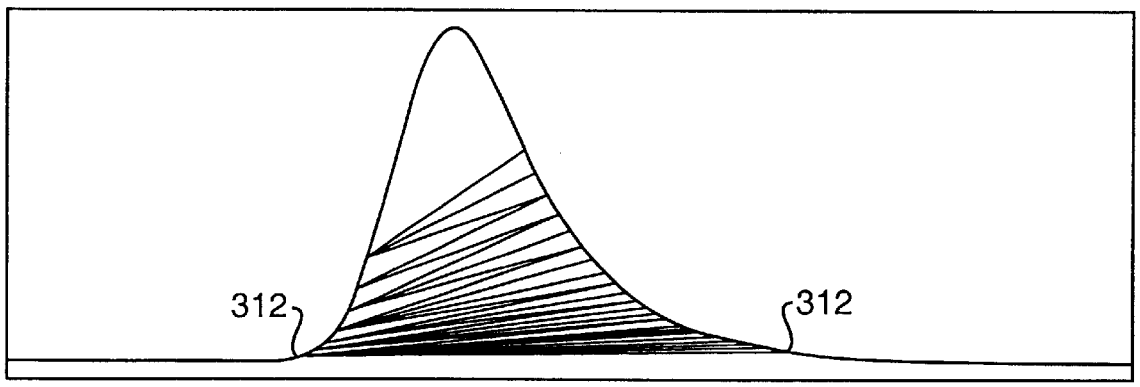
FIG. 3F shows all the lines drawn and a resulting final baseline.

The application of the above algorithm, as used within the inventive method, is depicted in FIGS. 3A through 3F. Referring to FIG. 3A, a line 301 is drawn connecting two inflection points, a point 302 on the up-slope and a point 304 on the down-slope of the apex. The line creates an up-slope angle 303 and a down-slope angle 305. The up-slope point 302 is the apex of the larger angle. Each angle is related to the difference between the slope of the line 301 and the slope of the profile at the point where the line 301 connects. As depicted in FIG. 3B, a new pair of points is selected. Because the up-slope point 302 has a smaller slope-difference it is retained. A new down-slope point 307 is selected and a new line 308 connects the two points. The time difference between the points corresponds to one sample period. As shown in FIG. 3C, the slope-difference on the down-slope is still larger and therefore a new down-slope point 309 is once again moved down. As shown in FIG. 3D, the slope-difference is now smaller on the up-slope side and so a new up-slope point 310 is selected. Referring to FIG. 3E, a new down-slope point 311 is selected, this method is continued until such time as the slope-difference reaches zero. FIG. 3F depicts all the lines drawn and the resulting final baseline. The final baseline is drawn between final end points 312. These points also determine the peak boundary for the purpose of quantitation.

The effect of this above procedure is to select the shortest baseline such that the baseline is tangent to the peak at its end points. The baseline is also independent of any slope added to the data, either mathematically or as the result of detector drift. The baseline has the same slope regardless of the height of the peak. The separation of the final baseline points will decrease as the height decreases, but this decrease will only reflect the fact that less of the peak lies above the baseline noise. Unlike the prior art the slope at the endpoints are considered simultaneously, not independently.

Figure 4A:
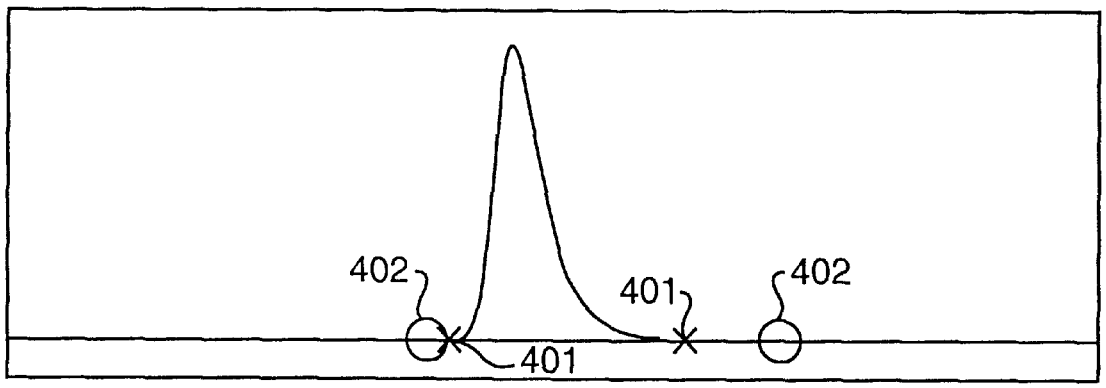
FIGS. 4A, 4B and 4C show the contrast of results obtained using the algorithm of the inventive method with that of results obtained using methods of the prior art.
Figure 4B:
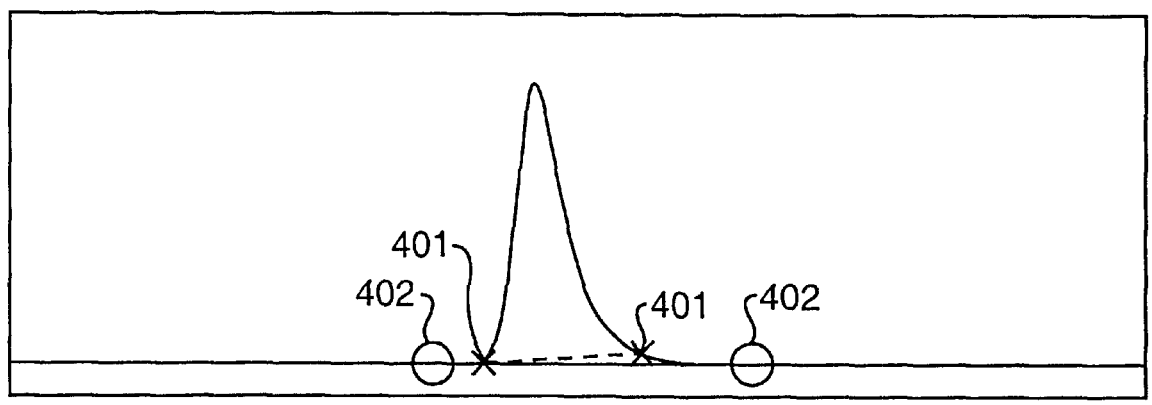
Figure 4C:
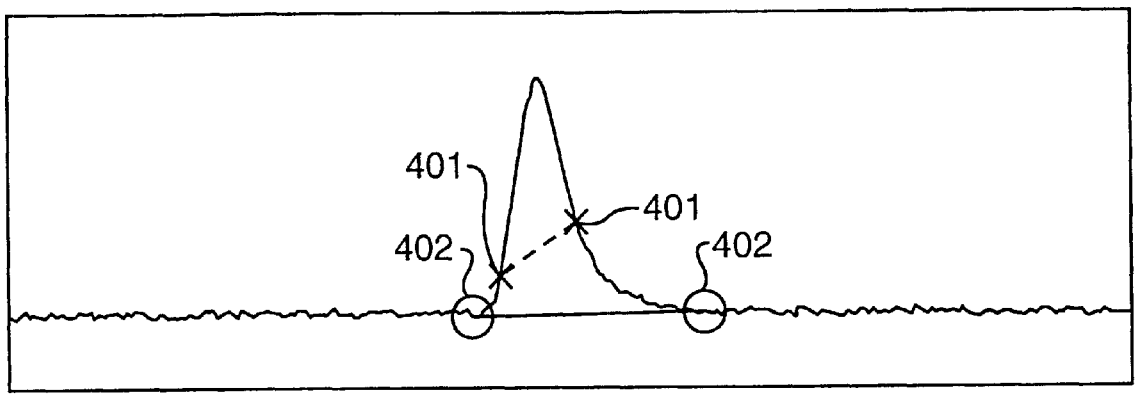

FIGS. 4A, 4B and 4C illustrate the contrast of results obtained using the algorithm of the inventive method with that of results obtained using methods of the prior art. As depicted in FIGS. 4A, 4B and 4C values 401 obtained using methods of the prior art are shown. The lift-off and touch-down times grow closer together and rise significantly above the baseline. Conversely, values 402 derived using the two-point tangent method identify start and stop times that stay within the baseline. The elution times of lift-off and touchdown move somewhat together as the peak height decreases, reflecting the fact that less of the peak is above the baseline noise.

Figure 5A:
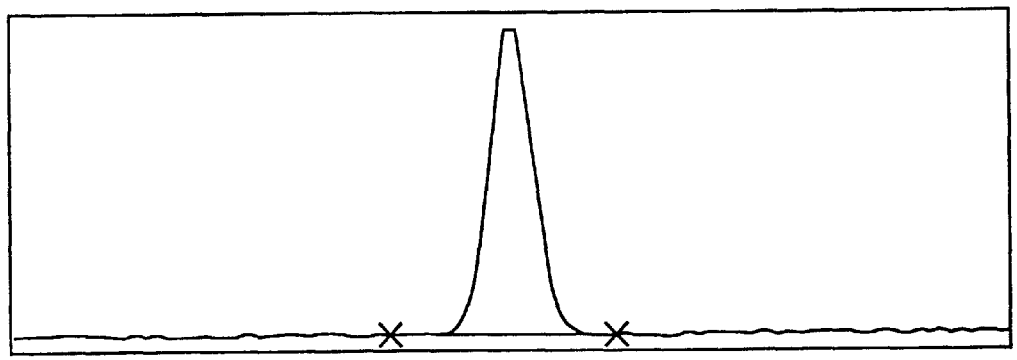
FIG. 5A shows a baseline determined for a 1 AU peak.
Figure 5B:
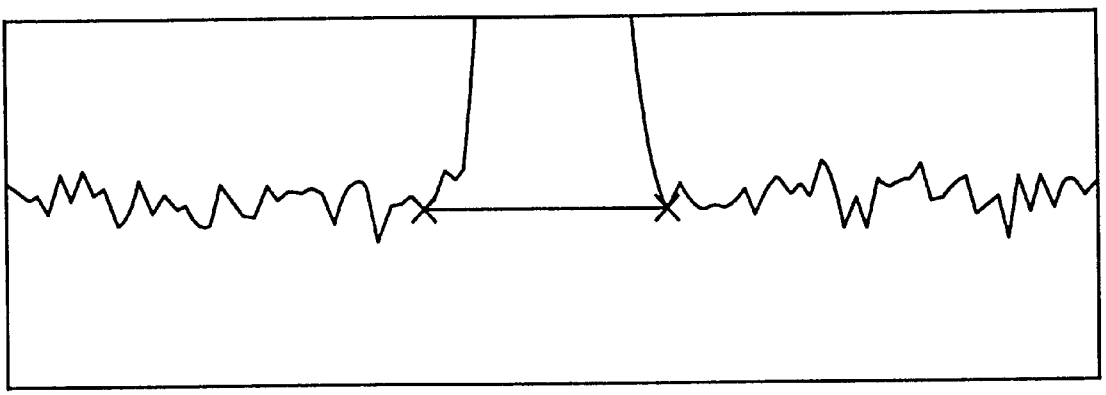
FIG. 5B shows how the tangency condition is satisfied.
Figure 5C:
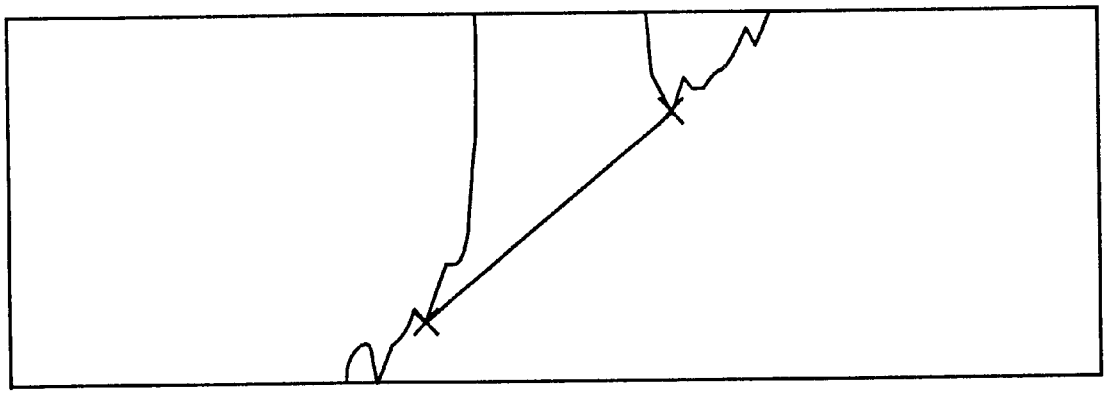
FIG. 5C shows a simulated sloped baseline.

FIGS. 5A and 5B illustrate that results obtained utilizing the inventive method are independent of the underlying baseline slope. FIG. 5A shows a baseline determined for a 1 AU (Absorbance Units) peak. FIG. 5B shows how the tangency condition is satisfied. FIG. 5C simulates a sloped baseline, this is accomplished by adding a ramp to each point. Applying the algorithm of the inventive method to such a peak yields a baseline drawn between the same points so the peak heights and areas are numerically the same value. The requirement that a reference line satisfy two slope conditions simultaneously defines the reference line so that its start and stop point is independent of the underlying baseline slope. The significance of this definition is apparent in FIG. 5C. If one simulates a baseline drift by adding to each point a ramp of constant slope, the slope of the line connecting these two points changes by exactly the same amount.

In an alternative illustrative embodiment a two-point fixed difference method is employed to determine the end points and hence the baseline. This method results in the shortest baseline such that the slope difference between the line and the end points are both equal to a preset threshold value. As in the two-point tangency method, inflection points are determined by finding the zero crossings of the second derivative that straddle the apex of the peak. Once the initial pair of points that connect the inflection points are located, then a slope-difference threshold is determined. The advantage of this method is that inclusion of the slope-difference threshold allows the baseline points to be closer together. This slope-difference threshold can be a fixed value or it can be determined by the properties of the peak under analysis. In one embodiment the slope-difference threshold equals the difference between the slopes of the profile found at the inflection points times a fractional value. Scaling the slope-difference threshold makes sure that these start and stop times remain independent of the peak height, as well as of the underlying baseline slope. The algorithm takes the initial pair of points that connect the inflection points and subjects them to the following method:

1. Determine a slope-difference threshold. This slope-difference threshold can be a fixed value, or can be determined by the properties of the peak under analysis. In one formulation, the slope-difference threshold equals the difference between the slopes of the profile found at the inflection points, times a fractional value. In an exemplary implementation, the fractional value is 0.5%, or 0.005. Thus the slope-difference threshold is 0.005 times the slope-difference.
2. Determine the slope of the line and the slope of the peak profile at the end points of the line.
3. Form two differences. The first difference is the difference between the peak slope on the up-slope at the end point minus the slope of the line. The second difference is the difference between the peak slope on the down slope at the end point minus the slope of the line. For the initial estimate, both these differences will be positive. The point with the larger difference is identified. If that difference is greater than the slope-difference threshold, then that point is moved outward by one sample point. Continue to step 4. If the difference is less than the slope-difference threshold, no further adjustments are made and the determination is finished. The start and stop times of the baseline is now determined as the final two points.

4. The two new points determine a new baseline.
5. Return to step 2.

Figure 6A:
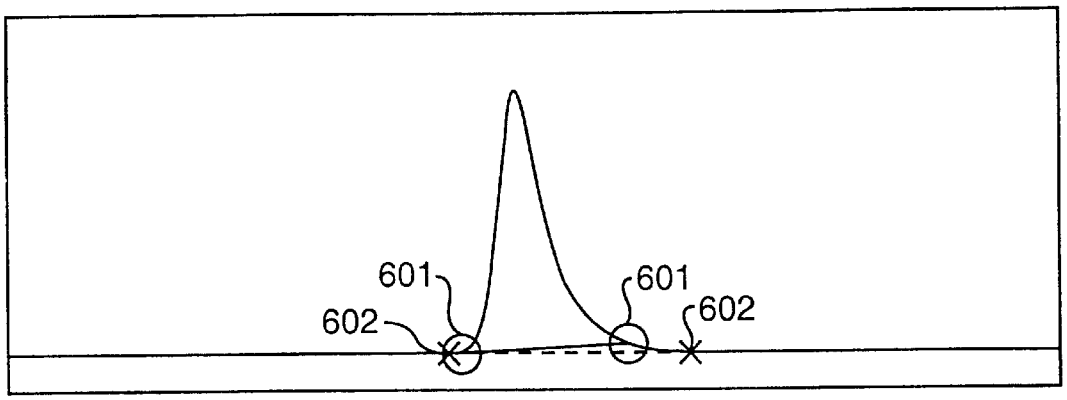
FIGS. 6A, 6B and 6C show the results of using a 0.5% fractional value.
Figure 6B:
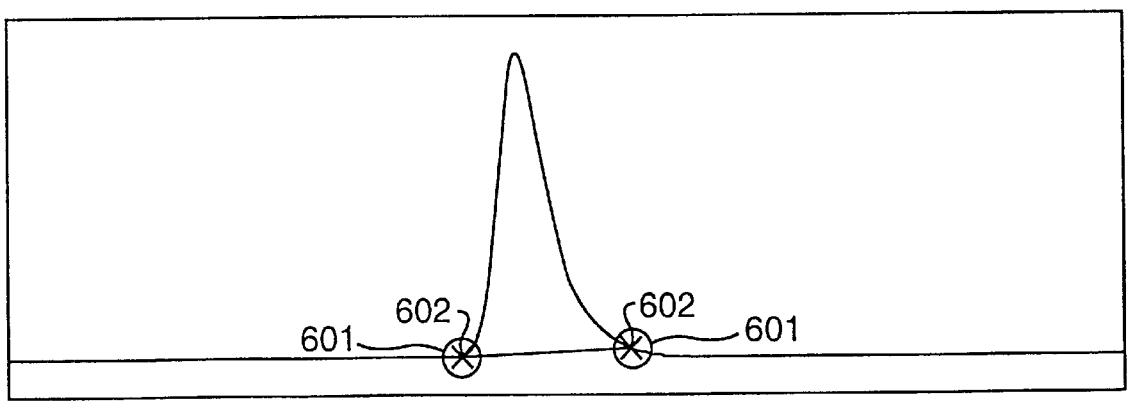
Figure 6C:
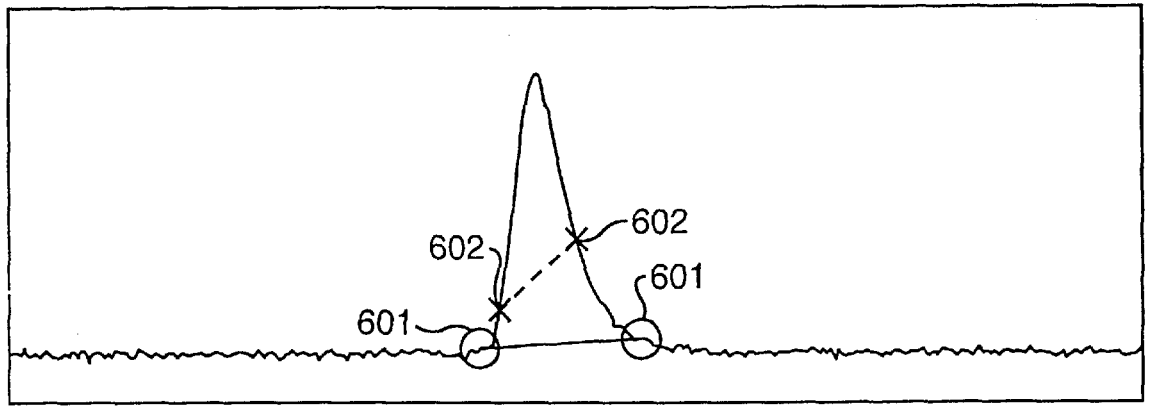

The two-point fixed difference method generates start and stop times that are closer together and more stable than in the two-point tangency method. These points are independent of the baseline noise, peak height and baseline slope. The results of using a 0.5% fractional value are shown in FIGS. 6A to 6C. The O-points 601 are obtained using the two-point fixed difference method. The X-points 602 are obtained using prior art methods.

Figure 7A:
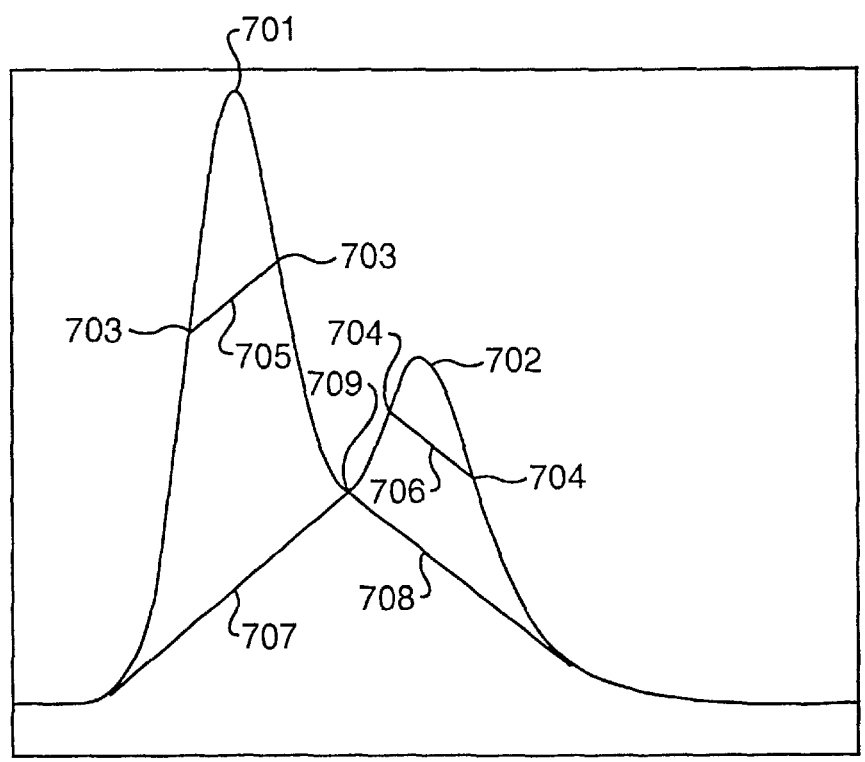
FIG. 7A shows a two peak cluster.

In chromatographic separations it is common for peaks to fuse and form clusters. The challenge of peak integration is to find a suitable cluster baseline. The start point of the cluster baseline is liftoff for the first peak and the end point is touch down for the last peak. FIG. 7A illustrates a two-peak cluster. Once again, the second derivative is used to identify the apices of the first peak 701 and the second peak 702. The second derivative is also used to identify the first peak's inflection points 703 and the second peak's inflection points 704. The first peak's inflection points 703 are connected with a first line 705. The second peak's inflection points 704 are connected with a second line 706. Either the two-point tangency method or the two-point fixed difference method can be used to locate a first baseline 707 for the first peak 701 and a second baseline 708 for the second peak 702. These baselines 707,708 are referred to as valley to valley baselines. The valley to valley baselines 707,708 do not correspond to a desired cluster baseline, however, they do intersect at a valley boundary 709 between the first peak 701 and the second peak 702. This intersection serves several purposes in that it identifies that the peaks are in fact overlapped and therefore identifies the peak boundary; this intersection also indicates that the baseline needs to be fused.

Figure 7B:
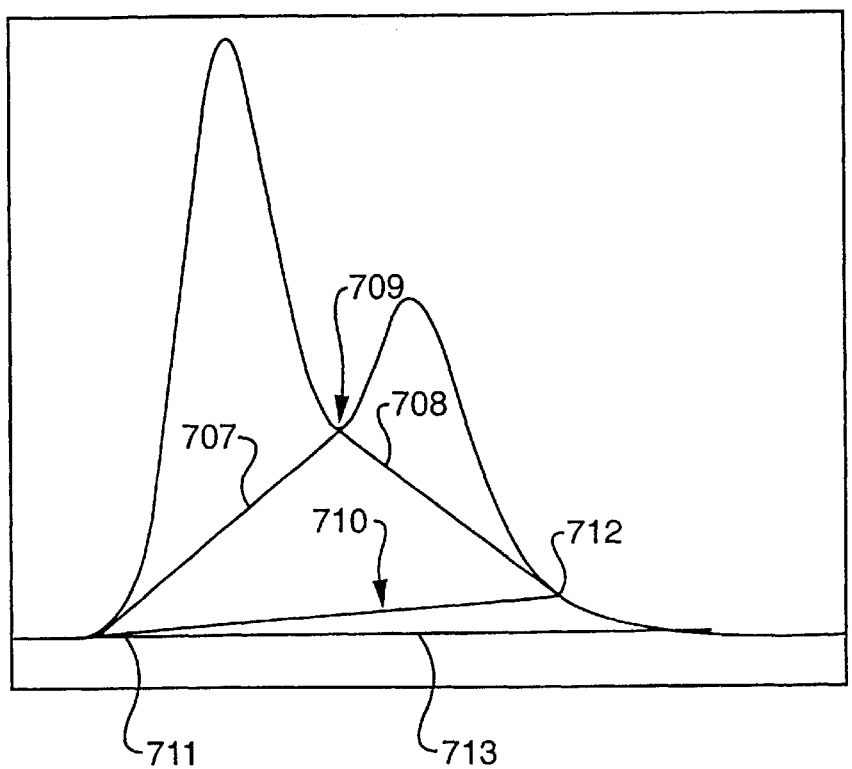
FIG. 7B shows a boundary and a overlap point.

Turning to FIG. 7B, the boundary and an overlap point 709 are depicted. The first baseline 707 and the second baseline 708 are replaced with a fused baseline 710. The fused baseline 710 has a starting point 711 that is the starting point of the first baseline 707. The fused baseline 710 has an ending point 712 that is the end point of the second baseline 708. Either the two-point tangency method or the two-point fixed difference method can be applied to the fused baseline 710 to produce a cluster baseline 713. The cluster baseline 713 is associated with the first peak 701 and the second peak 702.

This method of determining a cluster baseline can be directly extended to peaks that contain an arbitrary number of fused peaks in a cluster. Using this method, whenever an overlap is found, the two intersecting baselines are replaced by a fused baseline and the fused baseline is then extrapolated until the appropriate tangent or fixed difference is found. This procedure is repeated until all baseline end points have been determined by the tangent or fixed difference method until there are no further overlaps between adjoining baselines.

Figure 8:
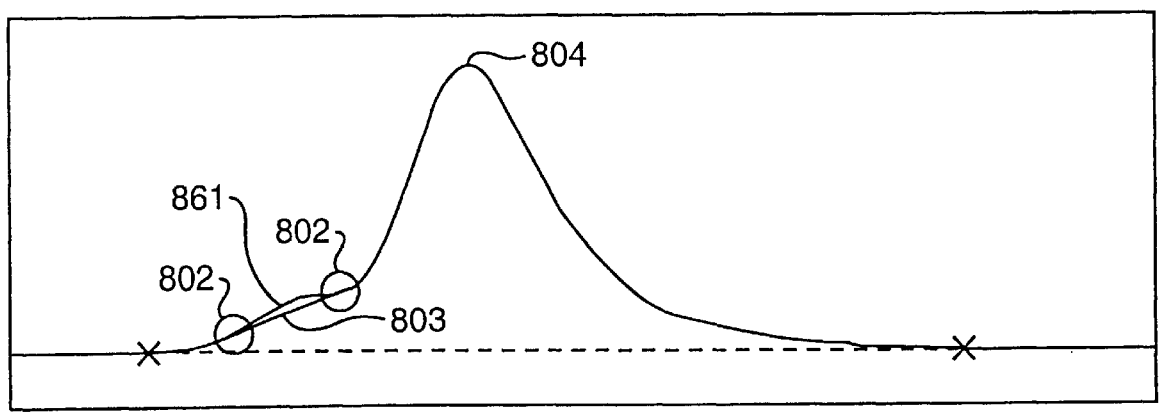
FIG. 8 shows an example of a fronting shoulder and its inflection points and a baseline found from those inflection points.

In chromatographic separations it is also common for peaks to have shoulders. Shoulders occur when peaks fuse at too low of a resolution to produce a valley point. While the apex detection routine will identify the apex and inflection points of a shoulder, the baseline found by either the two-point tangency or fixed difference method will not correspond to the shoulder, but rather, it will be associated with an adjacent peak. FIG. 8 shows an example of a fronting shoulder 801 and its inflection points 802 and a baseline 803 found from those inflection points 802. The challenge is how to demarcate a boundary between the shouldered peak 801 and an adjoining peak 804. In an illustrative embodiment, a one point tangent method is used to demarcate the boundary between the shouldered peak 801 and the adjoining peak 804. This method can be implemented in one of two ways and can be applied to any peak shouldered, isolated or adjoining a valley.

Figure 9:
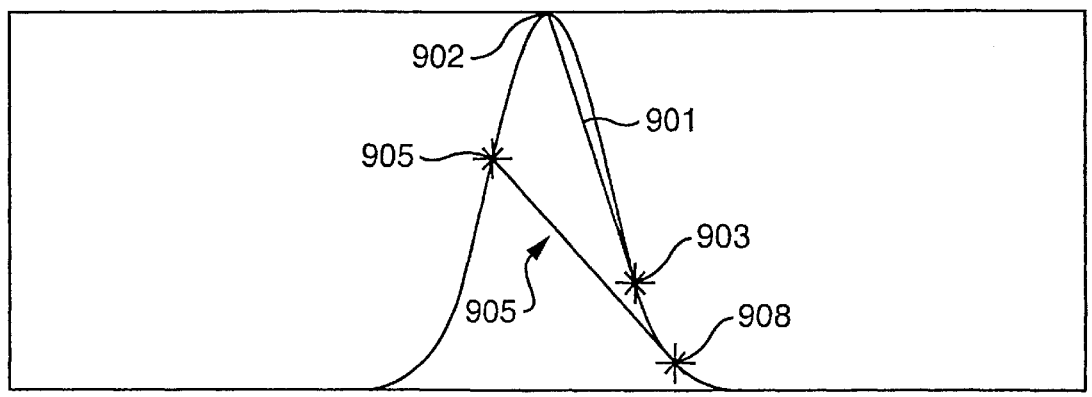
FIG. 9 shows two different one-point tangent methods.

One approach is the one-point-tangent method as shown in FIG. 9. The first implementation connects a line 901 from a point on the apex 902 to a downside point 903 on the down-slope side of the apex 902. The slope of the profile at the downside point 903 equals the slope of the line 901. The line 901 is tangent to the peak profile at the point of contact. The algorithm for finding the tangent point is straightforward. The initial line 901 connects the apex 902 to the down-slope inflection point. The point on the apex 902 remains fixed, while the point on the inflection point is moved away from the apex sample point by sample point. When the line first contacts the inflection point the slope of the line is less than the slope of the contact point on the profile. As the point moves away the slope of the line becomes larger resulting in a decrease of the slope at the contact point. When the slope of the line is equal to or greater than the slope at the contact point 903 the line is fixed.

The significance of the contact point is that it can be used as a peak boundary for peak integration and for fraction collection. In the case of peak integration, the contact point can be used to demarcate a shoulder from an adjoining peak. In the case of fraction collection, the contact point can be used to close a valve when the fraction is to be collected from the heart of the peak.

Using the above one-point method the time of the contact point is independent of both the slope of the baseline underlying the peak and of peak height. This independence results from the fact that the end point at the apex is obtained from the $2^{nd}$ derivative and the contact point is obtained by matching two slopes. Changing the underlying baseline slope leaves the contact point unchanged. In an alternative implementation, also depicted in FIG. 9, an initial line 905 connects an up-slope inflection point 906 and a downside inflection point. The up-slope inflection point 906 is fixed and the down-slope inflection point is moved until it becomes tangent to the peak 908. The resulting peak boundary using this second implementation is further down the peak. In yet a further alternative method, instead of moving the down-slope inflection point, the up-slope point 906 can be moved. The initial line 905 could be from the up-slope inflection point 906 to the apex 901 and the sample point 906 can be moved until a tangency is reached. In yet a further alternative method, the initial line 905 can connect both inflection points and it can then be moved until a tangency is reached.

In addition to quantitation, fraction collection is the second major application of chromatography. Unlike a peak integration algorithm, which is invoked after all the data is collected, a fraction collection algorithm is invoked while data is collected. In peak integration, algorithmic operations are applied in parallel and in fixed sequence. Conversely, in fraction collection, a complete analysis is performed each time a new data point arrives. The inventive method utilizes data from a single channel detector, such as that obtained from a UV absorbance or mass-spectrometric detector. This method is designed to determine start and stop times for the collection of fractions and can collect peaks that elute in both simple and complex separations, as well as collect shouldered peaks and small peaks on a wandering baseline.

Fraction collection systems require a processor that handles each new response as it is collected. Each response, which is referred to herein as a "datum," is separated by a fixed sample period. At the heart of the processor are algorithms that interpret each datum followed by a decision tree to determine what action, such as opening a valve, if any needs to be taken. The inventive fraction collection system described herein implements a feature detection system based on determining the smoothed, first and second derivatives associated with each new datum as it arrives. The decision tree is implemented by assigning to each new datum a state. The rules by which a state is assigned are formalized in a transition matrix. The state of the current datum depends on the state of the prior datum and input values. In the inventive method, these input values are values of the smoothed, first and second derivative chromatograms associated with current and prior data.

Specifically, the inventive method uses the maxima and minima of second derivatives and one-point tangent methods to identify the occurrence of key states critical to the collection of fractions. The maxima and minima of second derivatives and the one-point tangent methods are the same as those described in the peak integration method disclosed hereinbefore.

Unlike the fraction collection methods of the prior art, the use of the inventive method to identify key states allows fractions to be collected at times that are independent of the both the underlying baseline slope, as well as the height of the peak. Further, the inventive method rules are robust and can collect fractions in complex chromatograms.

Figure 10:
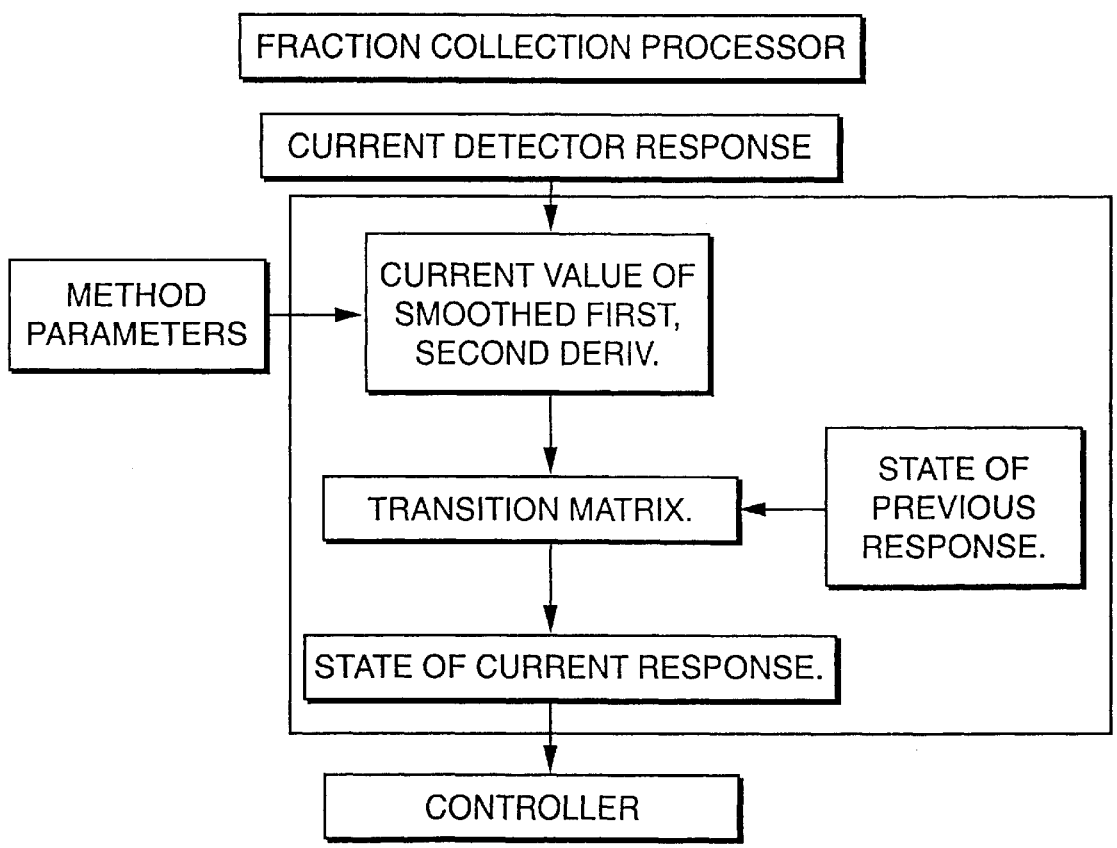
FIG. 10 is a flow diagram illustrating the operation of a Fraction Collection Processor.

Referring to FIG. 10, a flow diagram illustrates the operation of a Fraction Collection Processor, implementing novel rules in the Transition Matrix that use the maxima and minima of second derivatives and the point tangent methods as described hereinbefore according to the invention.

Within the Fraction Collection Processor, the arrival of a new datum causes the computation of the next point for a smoothed chromatogram, its first and second derivatives. These results can be obtained with moving average Finite Impulse Response (FIR) filters that process the data obtained in real time.

The Fraction Collection Processor uses these outputs to determine the state of the current point. Every datum is assigned a state. The state of the current point depends on the state of the prior point plus the current and prior input. A state transition matrix described hereinafter gives the rules by which the state of the current point is determined.

The Fraction Collection Processor retains all knowledge about the prior processed data and therefore the state of the prior point is always available, as are the prior responses as well as their smoothed, first and second derivative values. The state of the current point is passed to the controller, and it is this information that is used to help determine when to collect a fraction. The Fraction Collection Processor communicates information to a controller. The role of the controller is to manage the collection of fractions. It insulates the Fraction Collection Processor from the detailed management of the fluidics.

Two implementations of a Fraction Collection Processor are described herein. Case 1, describes a Fraction Collection Processor for collecting fraction when there is no overlap between peaks. Case 2 describes a Fraction Collection Processor that can handle a general chromatogram that contains both isolated and fused peaks.

Figure 11:
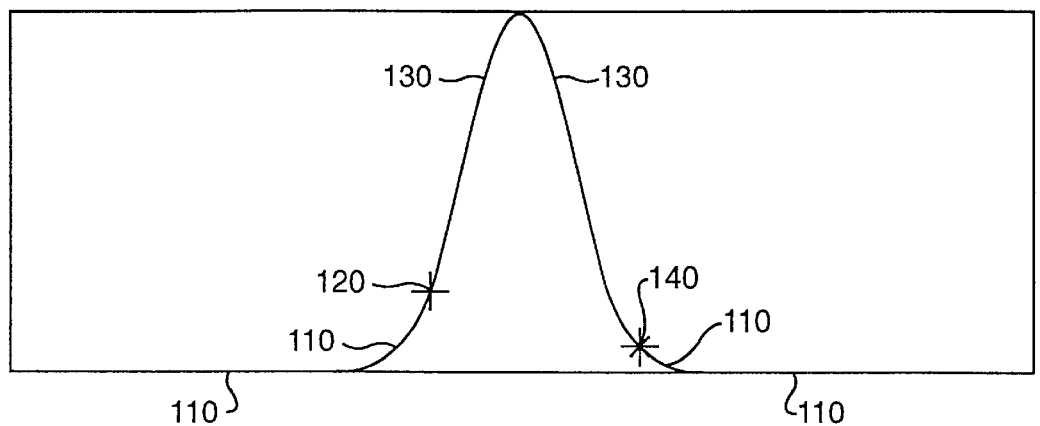
FIG. 11 shows isolated and single-point states and the states of the regions between them.

In the illustrative embodiment Case 1, four states are assigned to various points in a chromatogram. These assignments are illustrated in FIG. 11 as follows: NotInPeak 110, DetectStart 120, InPeak 130 and DetectEnd 140. The DetectStart 120 state is always followed by the InPeak state 130, and the DetectEnd state 140 is always followed by the NotInPeak state 110. DetectStart 120 and DetectEnd 140 are termed isolated states, since these states occur only at a single sample point.

NotInPeak 110 is a decision state, because it can be followed either by a NotInPeak 110 state or by a DetectStart 120 state. Analogously, InPeak 130 is also a decision state. It can be followed either by InPeak 130 state or by a DetectEnd 140 state.

All points that precede DetectStart 120 and follow DetectEnd 140 are NotInPeak 110 states. All points that follow DetectStart 120 and precede DetectEnd 140 are InPeak states 130. The controller can use two states, DetectStart 120 and DetectEnd 140, to direct the opening and closing of a valve. Thus, FIG. 11 illustrates the isolated, single-point states, and the states of the regions between them.

Figure 12A:
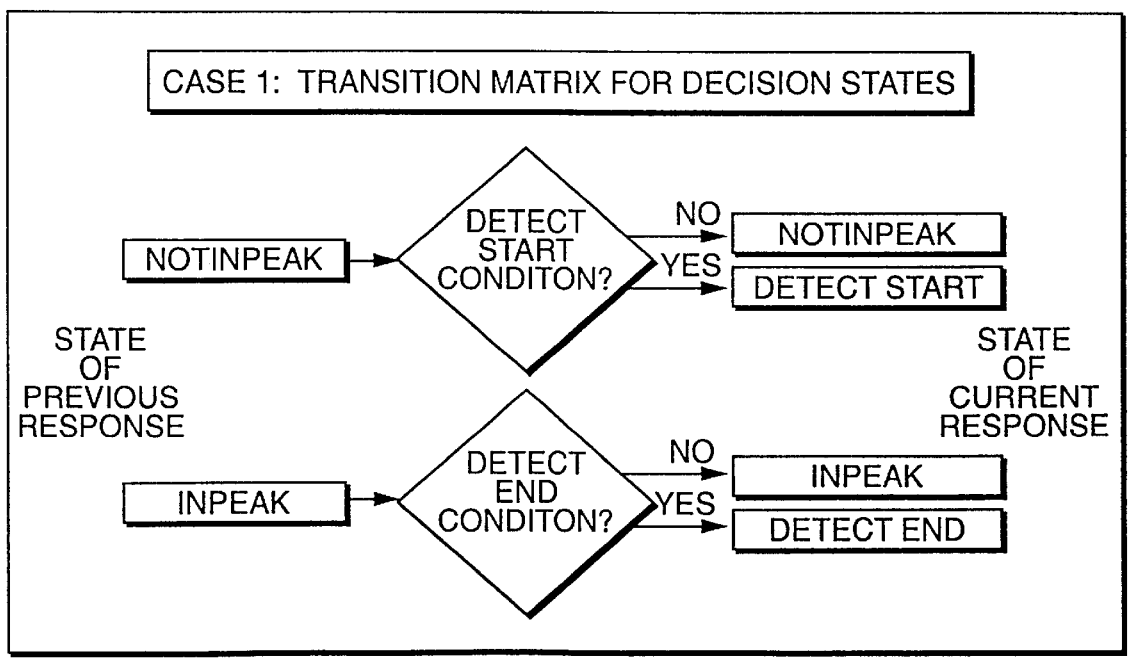
FIG. 12A shows a transition matrix for decision states.
Figure 12B:
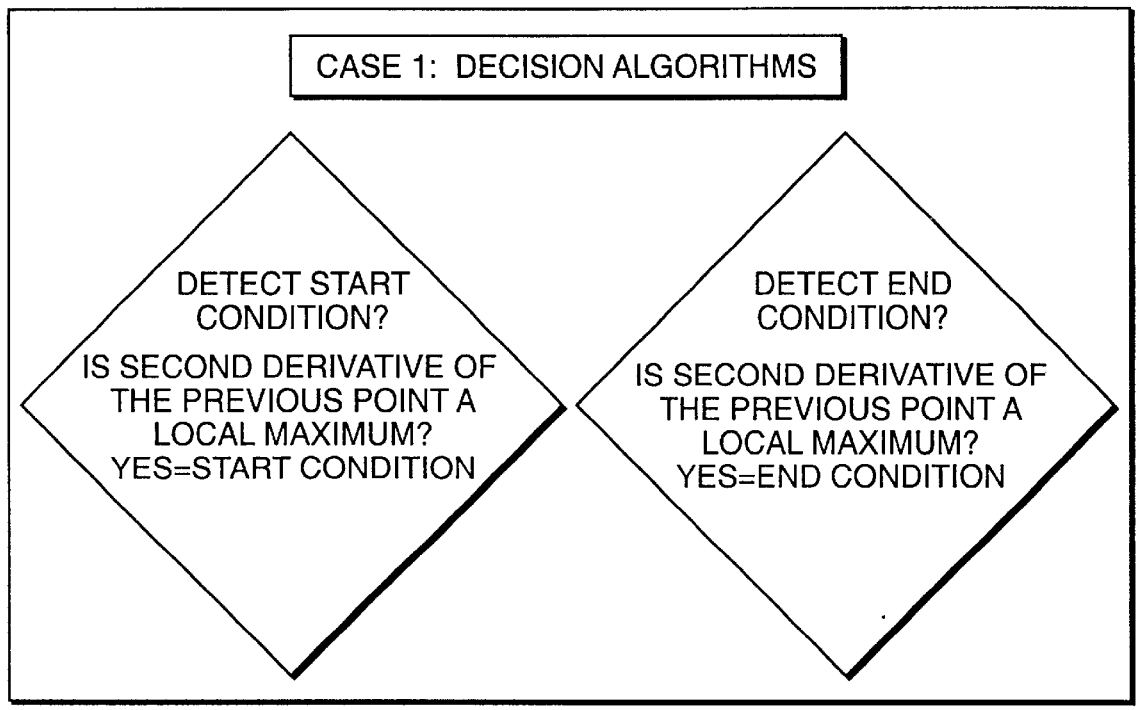
FIG. 12B shows decision algorithms for decision states.

Referring to FIGS. 12A and 12B, the transition matrix for the decision states and the associated decision algorithms are shown. In FIG. 12A, the states on the left are from the previous response and the states on the right are the current states.

In FIGS. 12A and 12B, the DetectStart condition is implemented by examining values for the second derivative. Given the second derivative of the current data point, one can determine if the previous datum was a local maximum of second derivative relative to its neighboring points.

Figure 12C:
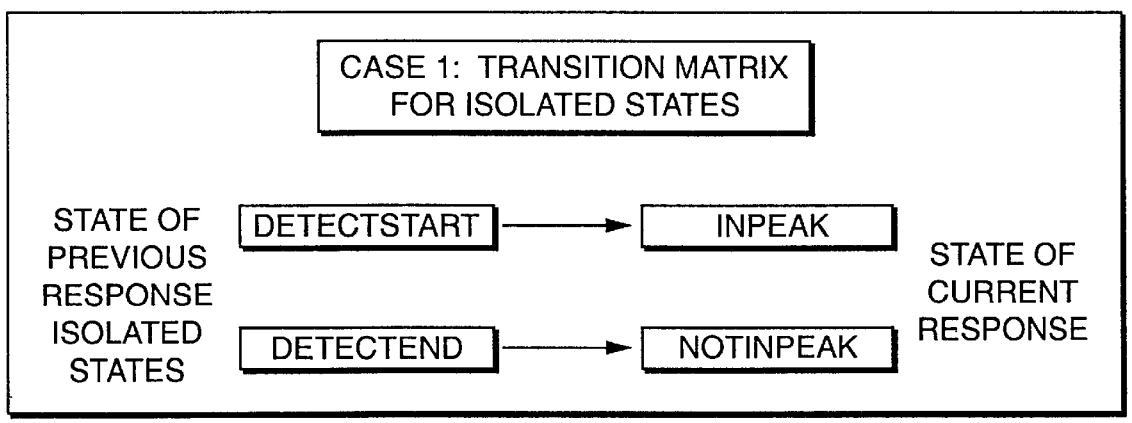
FIG. 12C shows a transition matrix for isolated states.

FIG. 12C shows the transition matrix for the two isolated States, DetectStart and DetectEnd. These states require no decision algorithm, since whenever such a state is obtained, the state of the following datum is determined by the rules in FIG. 12C.

Figures 12D, 13:
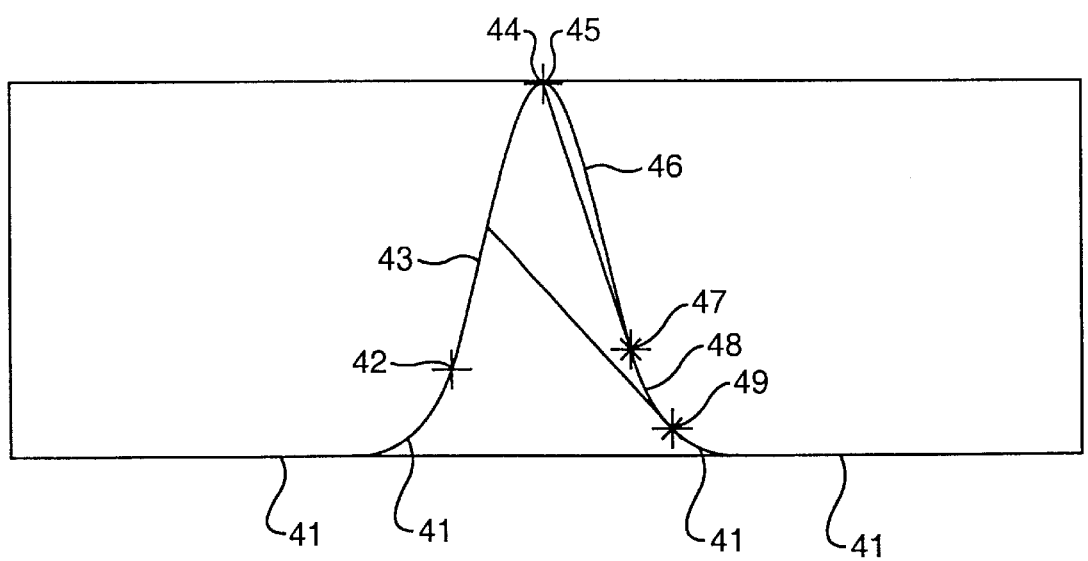
FIG. 12D is a table showing simplified allowed transitions between states.
FIG. 13 shows an isolated peak that contains states that the inventive method implements.

A more efficient manner in which to specify the transition matrix is to simply specify the allowed transition between states as displayed in FIG. 12D. All four allowed states are listed in the top row and in the first column. The states in the first column are previous sates. The states in the first row are the current states. Boxes having an (x) show allowed transitions.

In an alternative embodiment, Case 2 illustrates an embodiment of the inventive method where the transition matrix is more robust than the example above. Referring to FIG. 13 an isolated peak that contains all states that the inventive method implements is shown.

There are four states that are decision states and five states that are isolated states. Each isolated state is preceded by and is followed by a decision state. If the preceding state is a decision state, then the state of the current datum is that same state or one of the isolated states, depending on the results of a test. Thus the same decision state is repeated until the conditions for a particular isolated state is found.

The four decision states are as follows: NotInPeak 41, InUpSlope 43, InDnSlope 46 and InTail 48. The five isolated states are as follows: DetectUpSlopeStart 42, D2Apex 44, DetectD2Apex 45, DetectEndFromApex 47 and DetectEndFromInflect 49.

Figure 14:
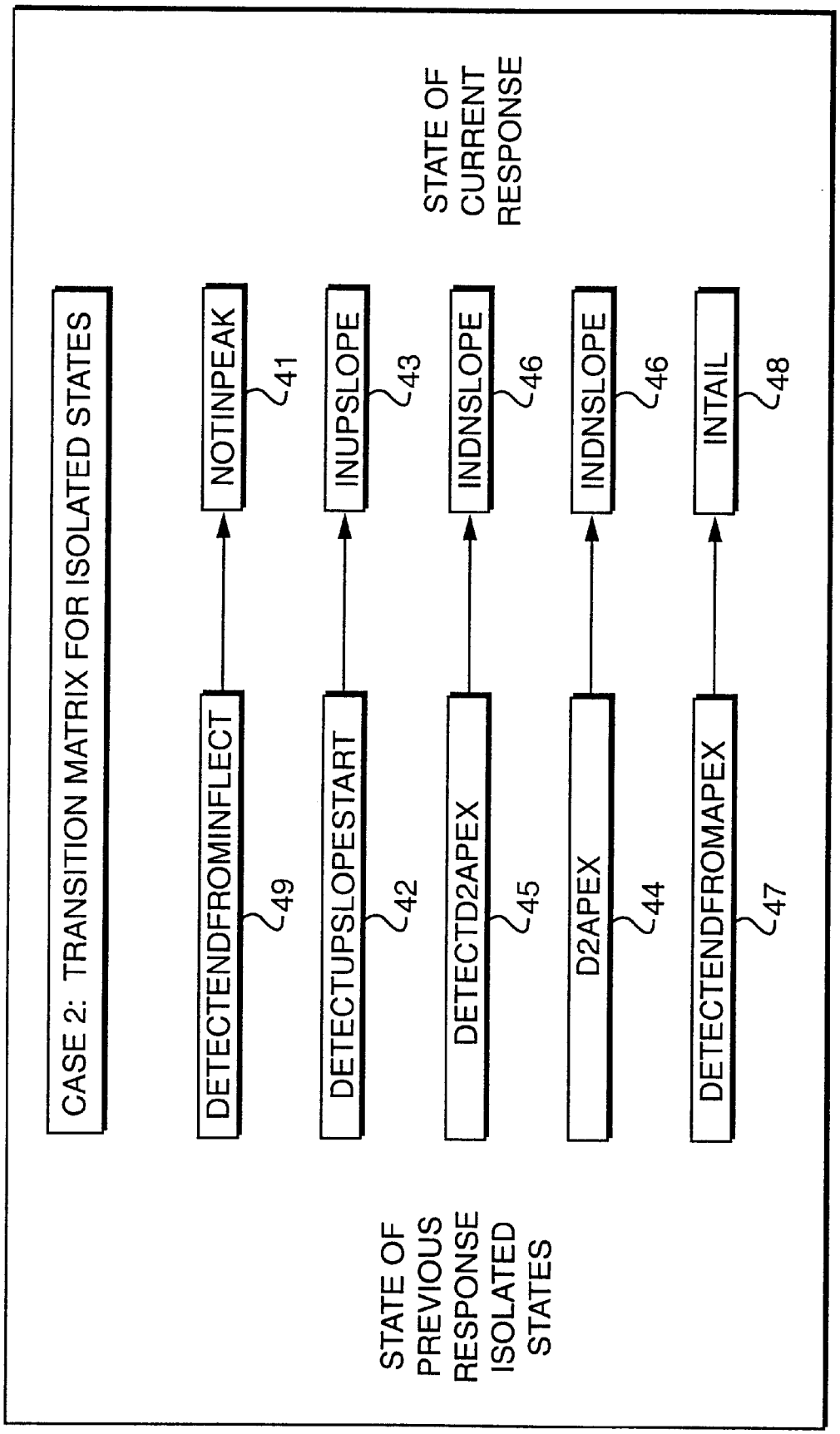
FIG. 14 shows a transition matrix for isolated states.

The transition matrix for the isolated states of Case 2 is shown in FIG. 14. These states require no decision algorithm, since whenever such a state is obtained, the state of the following datum is determined by rules shown in FIG. 14.

Figure 15A:
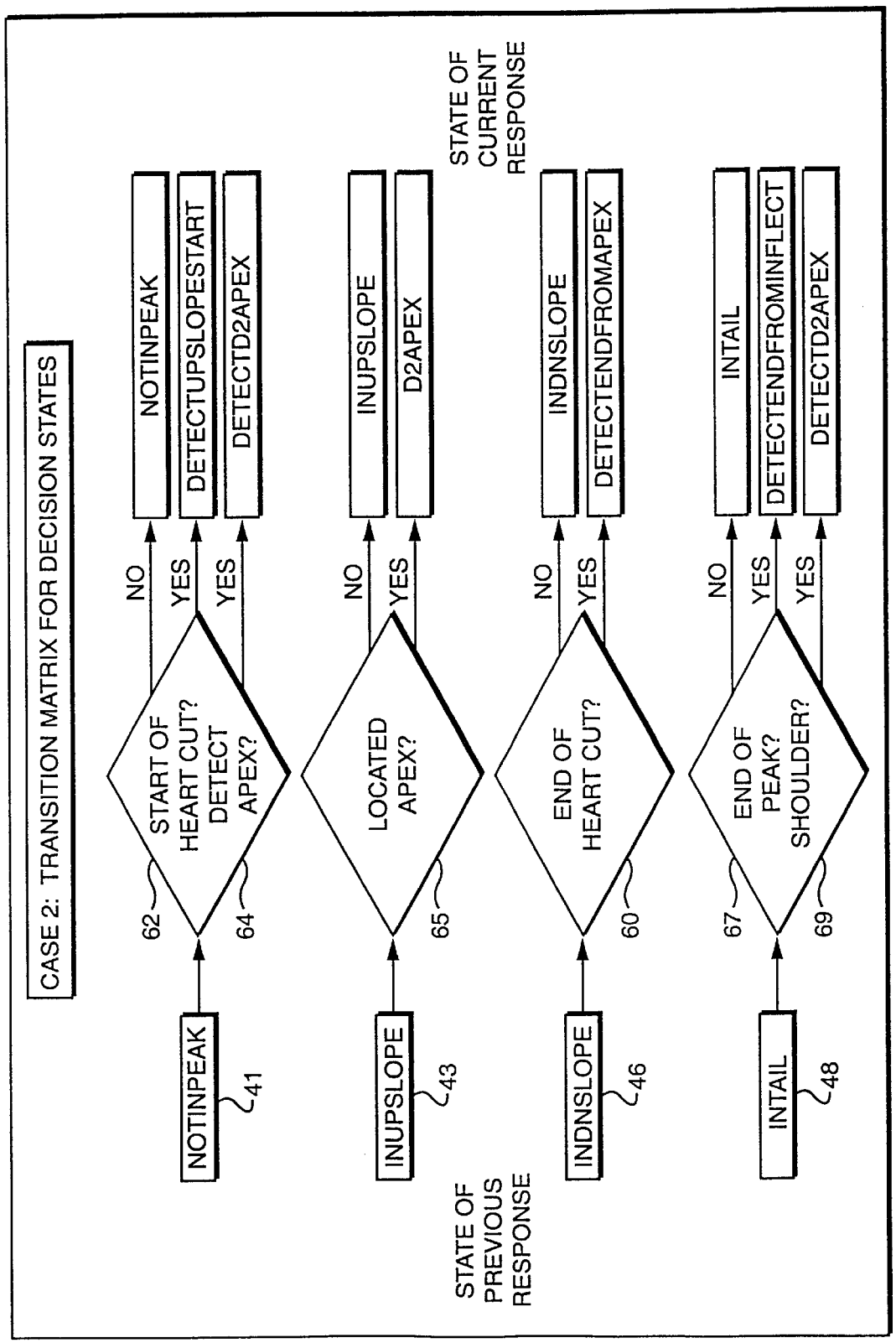
FIG. 15A shows a transition matrix for decision states.
Figure 15B:
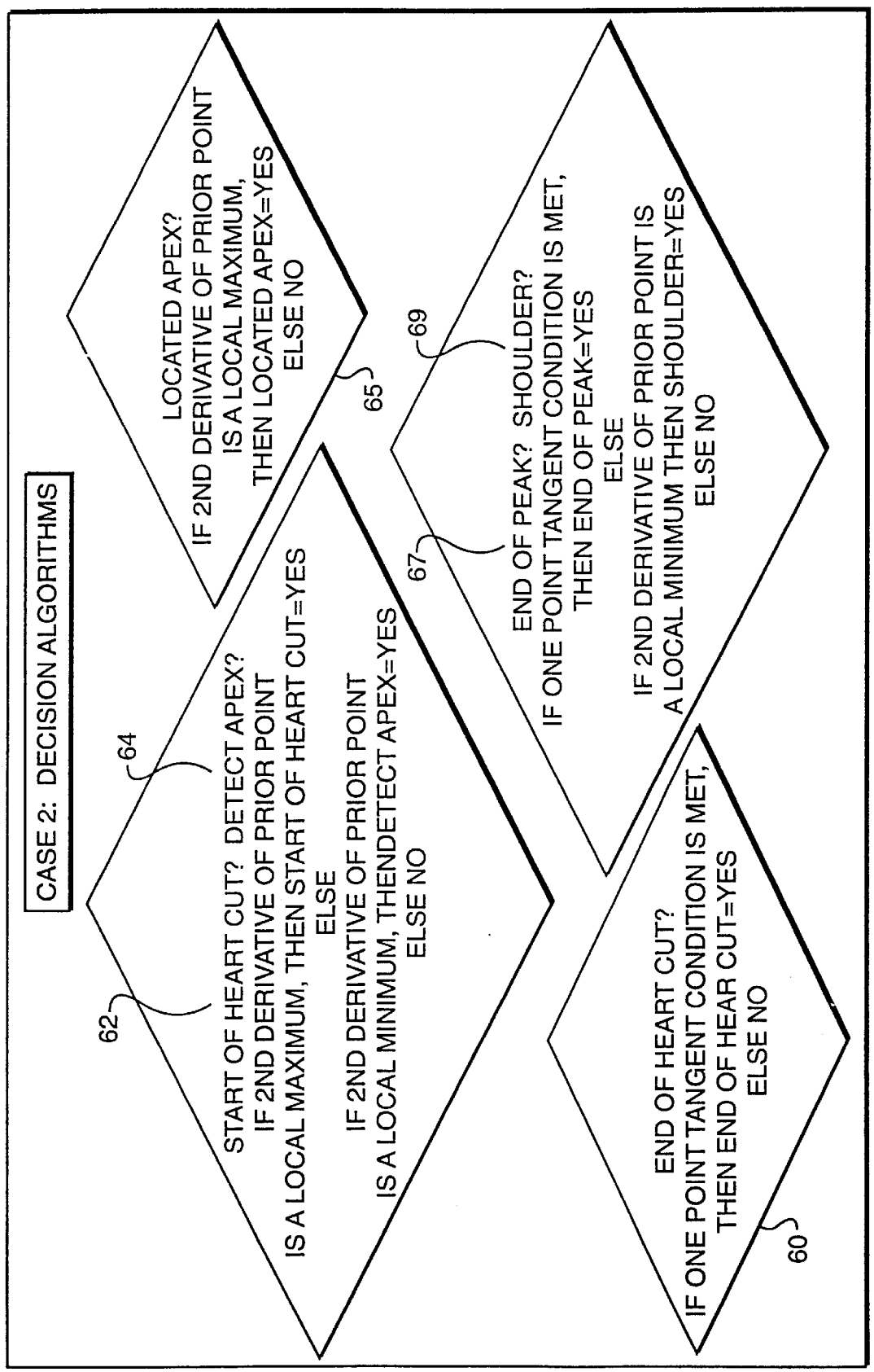
FIG. 15B shows decision algorithms for decision states.

The transition matrix for the decision states is depicted in FIG. 15A. The decision algorithms for the decision states are depicted in FIG. 15B.

Referring to FIG. 15A, the transition matrix calls out four decision states as follows: NotInPeak 41, InUpSlope 43, In DnSlope 46 and InTail 48. These decision states make use of the methods described as part of the peak integration method and are specified in FIG. 15B. The Start of Heart Cut? 62 is a test that identifies the start of the peak as the first local minimum of the second derivative, whose magnitude is above a predetermined threshold. The Detect Apex? 64 is a test that identifies the apex of the peak as a local maximum of $2^{nd}$ derivative as encountered in the NotIPeak 41 state. This test is needed for low-level peaks that are not detected by the Start of Heart Cut? 62 test. The Located Apex? 65 identifies the apex of the peak when a local maximum of $2^{nd}$ derivative is encountered during the InUpSlope state. The End of Heart Cut? 60 identifies the end of the heart of the peak by the one-point tangent method, Apex-tangent. The End of Peak? 67 identifies the end of the peak by the one-point tangent method, Inflection-point tangent. The Shoulder? 69 is determined when a local maximum of $2^{nd}$ derivative is encountered during the InTail state. The InTail state, which invokes the Shoulder? test, is needed to handle shouldered peaks on a down-slope that can occur before the end of a peak is reached.

As with any state matrix, the key input is the state of the previous point. The utility of the state machine approach arises because the job of the transition processor is limited to determining which of only a handful of states to assign to the current point. The state of the previous point then acts as a switch that points to a relatively small subset of decision making code. The complete set of states and the matrix of allowed transitions (X) are displayed in FIG. 16.

Within the inventive method, the job of the controller is to manage the collection of fractions. The controller takes as input the state of the current point. The controller may well have other user- or system-directed inputs needed to manage the physical fraction collector, which are beyond the scope of the present invention.

An example of how the controller can use the information from the Fraction Collection Processor, one can consider the case where a user wants to obtain 100% recovery of all peaks. The controller could use the one-in-a-row states DetectUpSlopeStart and DetectEndFromInflect to open and close valves. The controller can also close valves at times that can be offset from the times of these states. Because there is often tubing inserted between the end of a detector and a fraction collector to produce a delay, the time of a state as determined by the Fraction Collection Processor may precede the time that portion of the eluent reaches the fraction collector. Thus when a DetectUpSlopeStart state is encountered, the controller may open a collection valve at an earlier time so as to obtain 100% recovery. If it is desired to collect from the heart of the peak, then the one-in-a-row states DetectUpSlopeStart and DetectEndFromApex can be used to open and close valves. Again, the actual times of valve open and close can be offset from the times of these states by a predetermined amount.

Figure 17:
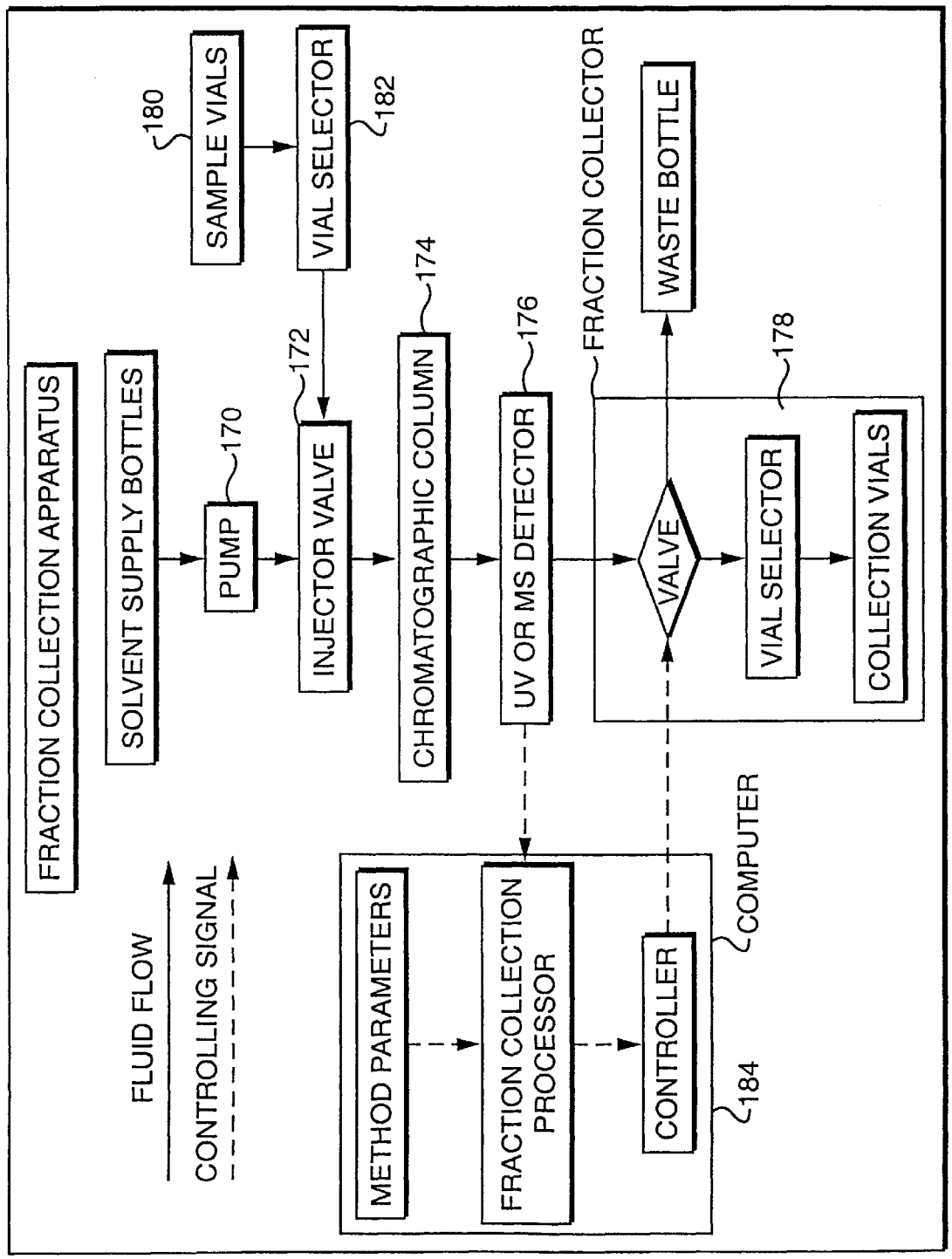
FIG. 17 is a block diagram of a Fraction Collection Apparatus according to the invention.

An illustrative implementation of a Fraction Collection Apparatus according to the invention is illustrated in FIG. 17.

The fraction collector apparatus is the combination of a chromatographic system followed by a fraction collector and appropriate control software. The apparatus comprises a pump 170, such as a Waters 2525 Binary Gradient Module, known in the art and available from Waters Corp, Milford, Mass. The pump is followed by an injector valve 172 in the fluidic stream, such as any of various known injector valves, delivering fluid to a chromatography column 174, such as an Xterra® Prep Column available from Waters Corp. Mobile phase through the fluidic stream is delivered to detector(s) 176 as a function of the application, such as a Waters 2487 Dual wavelength Absorbance Detector, or Waters 2996 Photodiode Array Detector, or Waters ZQ Mass Detector. Fraction Collector components 178 can be implemented in a system such as Waters 2767 Sample Manager which contains the Fraction Collector comprising valve, vial selector, and collection vials. It should be appreciated that such a system comprises, as well, Sample Vials, a Vial Selector, and the Injector Valve.

The illustrative chromatographic system consists of the sample vials 180, each vial containing a mixture to be fractionated. There is a mechanism to select one vial 182, and a mechanism (involving a valve) to inject some or all of the vial's contents into a flowing solvent stream. The Waters 2767 Sample manager is only one example of a system that contains the vials, selector mechanism, and injector mechanism. The solvent stream is supplied from one or more solvent bottles. The stream can be of a fixed composition (isocratic separation) or a composition that varies in time (gradient separation). The pump 170 causes the solvent and the injected mixture to flow through the chromatographic column 174. The Waters 2525 Binary Gradient Module is only one example of a pump that can cause a mixture consisting of a variable composition of two solvents to flow through the column. The eluent flowing out of the column 174, containing the separated components of the mixture, flows through a detector 176. Again, the detector can be a UV absorbance detector such as a Waters 2487 Dual Wavelength Absorbance Detector, or a Waters 2996 Photodiode Array Detector. The detector can also be a Waters ZQ Mass Detector that is used in place of, or downstream of, the UV detector. In order to collect fractions using a mass spectrometer, only a portion of the eluent stream will be directed through the mass spectrometer, since the material injected into the mass spectrometer is destroyed.

In chromatographic systems used only for analytic purposes, where only peak heights or areas are to be measured, the eluent flows to a waste bottle (in the case of UV detection) or into the vacuum system of the mass spectrometer (in the case of MS detection). In a fraction collection apparatus, the detector is followed by a fraction collector. The fraction collector is comprised of the valving system, vial selector, and collection vials 178.

The fraction collector can accept commands from a computer 184. Such a computer will include control software (i.e. controller), such as MassLynx Software and/or FractionLynx Application Manager which will contain Method Parameters, Fraction Collection Processor and Controller, all as known in the art and available from Waters Corp. Typically these commands consist of start collection, end collection, and move to a new collection vial. Start collection causes the eluent to collect in a pre-selected collection vial. Stop collection causes the eluent to flow to the waste bottle. Move to a new collection vial causes the fraction collection mechanism to translate to a new vial in the bed of collection vials. An example of a fraction collector is also contained within the Waters 2767 Sample Manager.

The computer 184 contains software both to control the chromatographic system (the pump, injector, and detectors)

as well a software to control the fraction collector hardware. This software is implemented in MassLynx Software and the FractionLynx Application Manager, both are implemented, for example, on a PC running Microsoft Windows. The MassLynx Software by itself is a general purpose chromatography mass-spectrometer application program. The FractionLynx Application, currently commercialized, controls the collection of fractions.

The three software components that will be implemented in any fraction collection apparatus are the Method Parameters, the Fraction Collection Processor, and the Controller. The methods described hereinbefore effectively replace two parts of the software currently implemented in the FractionLynx Application software. These would be the Method Parameters section, and the Fraction Collector Processor. The Controller software which handles the details of giving commands to the Fraction Collector is largely unchanged.

In operation, the fraction collection apparatus separates a mixture and, in response to the detector output, collects portions of the eluent into vials. At regular sample intervals, the detector transmits a response to the computer, and at each interval, the Fraction Collector Processor reports a state to the Controller.

The Controller is separately programmed to determine whether to open/close a valve, or to move to a new vial.

Generally there is a several second delay for fluid to flow between the detector and the valve in the fraction collector. The controller takes into account this delay when determining when to open or close a valve. Such software in the controller is as known in the art.

To collect at the heart of the peak, the Controller can be programmed, as described hereinbefore according to the invention, to open a valve that fixed time after it receives a DetectUpSlopeStart state from the Fraction Collector Processor. The Controller will close the valve at a fixed time after it receives the DetectEndFromApex state. After the valve is closed, the controller can issue a command to move the fraction collection mechansim to a new vial.

To collect 100% of the material, the Controller can be programmed to open a valve shortly after it receives a DetectUpSlopeStart state. The Controller will close the valve at a time after it receives the DetectEndFromInflect state, since this state occurs further down the peak after the DetectEndFromApex state. Again, after the valve is closed, the Controller can issue a command to move the fraction collection mechansim to a new vial. Additional rules can be programmed, as described, to account for collection of shoulders and to take into account the full spectrum of states that can be reported by the Fraction Collection Processor.

Although embodiments of the present method are described in applications wherein the detector response profiles are chromatographs, it should be appreciated that the detector response profiles can be obtained from one or more of various other types of detectors, including absorbance detectors, fluorescence detectors, mass spectrometry detectors, chemi-luminescence detectors, refractometry detectors, viscometry detectors, radiation detectors and thermometers.

The foregoing describes specific embodiments of the inventive method and apparatus. The present disclosure is not limited in scope by the illustrative embodiments described, which are intended as specific illustrations of individual aspects of the disclosure. Functionally equivalent methods and components are within the scope of the disclosure. Indeed, the instant disclosure permits various and further modifications to the illustrative embodiments, which will become apparent to those skilled in the art. Such modifications are intended to fall within the scope of the appended claims.

What is claimed is:

1. A method for determining the boundary of a peak of a detector response profile said peak corresponds to a chemical entity flowing through a conduit, the method comprising the steps of:

determining the presence of a peak having an apex and two sides;

selecting a first data point and a second data point;

determining a slope-difference threshold wherein the slope-difference threshold can be a fixed value, or can be determined by the properties of the peak under analysis;

determining a slope of a line and a slope of a peak profile at the first data point and a second data point of the line;

forming a first difference and a second difference wherein the first difference is the difference between a peak slope on an up-slope at the data point minus a slope of the line and the second difference is the difference between a peak slope on a down slope at the data point minus the slope of the line;

identifying the data point with the larger difference; wherein if that difference is greater than a slope-difference threshold, then that point is moved outward by one sample point and if the difference is less than the slope-difference threshold, no further adjustments are made; and determining a baseline by the final data points.

2. The method of claim 1 wherein the slope-difference threshold equals the difference between the slopes of the profile found at the data points, times a fractional value.

3. The method of claim 2 wherein said boundary of a detector response profile is an isolated peak.

4. The method of claim 1 wherein said detector response profiles are chromatographs.

5. The method of claim 1 wherein said detector response profiles are obtained from one or more of the group consisting of absorbance detectors, fluorescence detectors, mass spectrometry detectors, chemi-luminescence detectors, refractometry detectors, viscometry detectors, radiation detectors and thermometers.

6. The method of claim 1 wherein said conduit has one or more valves that can direct the chemical entity to a further conduit, vessel or vents, said method further comprising the step of opening one or more valves to direct said chemical entity into said further conduit, vessel or vent.

7. The method of claim 1 wherein said boundary of a detector response profile is a cluster of peaks.

8. The method of claim 1 wherein said boundary of a detector response profile is a cluster of peaks.

9. A method for determining the boundary of a peak of a detector response profile using a programmable computer system said peak corresponds to a chemical entity flowing through a conduit, the method comprising the steps of:

determining the presence of a peak having an apex and two sides;

selecting a first data point and a second data point;

determining a slope of a line between the first data point and the second data point;

forming a first difference and wherein the first difference is the difference between a peak slope on an upslope at the first data point minus the slope of the line;

forming and a second difference wherein the second difference is the difference between the peak slope on a down slope at the second data point minus the slope of the line;

identifying the larger of said first difference and said second difference to determine a greater difference if said greater difference is greater than zero then that data point is moved outward by one sample point forming a next data point, if the difference is less than zero, no further adjustment is made and a last two data points on the upslope and the downslope are identified; and determining the start and stop times of the baseline by using the last two data points.

10. The method of claim 9 wherein said peak is detected by computing the second derivative of the plot to form a second derivative plot and identifying a minimum of the second derivative plot said minimum of the second derivative plot corresponds to the apex of the peak of the plot.

11. The method of claim 9 wherein said detector response profiles are chromatographs.

12. The method of claim 9 wherein said detector response profiles are obtained from one or more of the group consisting of absorbance detectors, fluorescence detectors, mass spectrometry detectors, chemi-luminescence detectors, refractometry detectors, viscometry detectors, radiation detectors and thermometers.

13. The method of claim 9 wherein said conduit has one or more valves that can direct the chemical entity to a further conduit, vessel or vents, said method further comprising the step of opening one or more valves to direct said chemical entity into said further conduit, vessel or vent.

14. The method of claim 9 wherein said boundary of a peak of a detector response profile is an isolated peak.

15. The method of claim 9 wherein said boundary of a peak of a detector response profile is a cluster of peaks.

16. A method of demarcating a boundary between a shouldered peak and an adjoining peak of a detector response profile wherein said shoulder peak and said adjoining peak correspond to chemical entities flowing through a conduit, the method comprising the of:

connecting a line from a first data point on an apex to a second data point on a downside point on said apex; and moving the second data point away from the apex point by point, wherein the slope of the line is equal to or greater than the slope of the line at the first data point.

17. The method of claim 16 wherein said first point remains fixed.

18. The method of claim 16 wherein said first data point is independent of both the slope of the baseline and peak height.

19. The method of claim 16 wherein said first data point is obtained from the $2^{nd}$ derivative of the apex of the peak.

20. The method of claim 16 wherein said first data point is an up-slope inflection point that is fixed and said second data point is a downside inflection point that is moved until it becomes tangent to the peak.

21. The method of claim 16 wherein said first data point is an up-slope inflection point that is fixed and said second data point is a downside inflection point that is moved until it becomes tangent to the peak.

* * * * *

UNITED STATES PATENT AND TRADEMARK OFFICE
CERTIFICATE OF CORRECTION

PATENT NO. : 6,694,265 B2
DATED : February 17, 2004
INVENTOR(S) : Marc V. Gorenstein It is certified that error appears in the above-identified patent and that said Letters Patent is hereby corrected as shown below:

Column 18,
Line 49, cancel"8. The method of claim" to and including "cluster of peaks."
Line 50, insert the following claim:
-- 8. The method of claim 1 wherein said boundary of a detector response profile is a peak with a shoulder. --

Signed and Sealed this

Twenty-fifth Day of May, 2004

JON W. DUDAS
*Acting Director of the United States Patent and Trademark Office*